United States Patent
Creelman et al.

(10) Patent No.: US 10,047,372 B1
(45) Date of Patent: Aug. 14, 2018

(54) NITROGEN UPTAKE IN PLANTS

(71) Applicant: Koch Biological Solutions, Inc., Hayward, CA (US)

(72) Inventors: Robert A. Creelman, Castro Valley, CA (US); Suqin Cai, Fremont, CA (US); Hans E. Holtan, Emeryville, CA (US); T. Lynne Reuber, San Mateo, CA (US); Oliver J. Ratcliffe, Oakland, CA (US)

(73) Assignee: Koch Biological Solutions, LLC, Hayward, CA (US)

( * ) Notice: Subject to any disclaimer, the term of this patent is extended or adjusted under 35 U.S.C. 154(b) by 261 days.

(21) Appl. No.: 14/645,030

(22) Filed: Mar. 11, 2015

Related U.S. Application Data

(60) Provisional application No. 61/951,934, filed on Mar. 12, 2014.

(51) Int. Cl.
*C12N 15/82* (2006.01)

(52) U.S. Cl.
CPC ..... *C12N 15/8261* (2013.01); *C12N 15/8227* (2013.01)

(58) Field of Classification Search
None
See application file for complete search history.

(56) References Cited

U.S. PATENT DOCUMENTS

2007/0033671 A1* 2/2007 Jiang .................. C07K 14/415 800/278

OTHER PUBLICATIONS

Engelbrecht et al 2004 (BMC Genomics 5:39 p. 1-17).*
K.G.Cassman, A. Dobermann, D.T. Walters. Agroecosystems, Nitrogen-use Efficiency, and Nitrogen Management. 2002. Ambio 31:132-140.
C. Diaz et al. Nitrogen Recycling and Remobilization Are Differentially Controlled by Leaf Senescence and Development Stage in *Arabidopsis*. 2008. Plant Physiol. 147:1437-1449.
A.D.M. Glass et al. The regulation of nitrate and ammonium transport systems in plants. 2002. J. Exp. Bot. 53:855-864.
A.G. Good et al. Can less yield more? Is reducing nutrient input into the environment compatible with maintaining crop production? 2004. Trends Plant Sci. 9:597-605.
A. Hodge, D. Robinson, A. Fitter. Are microorganisms more effective than plants at competing for nitrogen? 2000. Trends Plant Sci. 5:304-308.
D.W.Lawlor. Carbon and nitrogen assimilation in relation to yield: mechanisms are the key to understanding production systems. 2002. J. Exp. Bot. 53:773-787.
F.I.M. Maathuis. Physiological functions of mineral macronutrients. 2009. Curr. Opin. Plant Biol. 12:250-258.
C.M. Masclaux-Daubresse et al. Nitrogen uptake, assimilation and remobilization in plants: challenges for sustainable and productive agriculture. 2010. Ann. Bot. 105:1141-1157.
B.E. Maust, J.G. Williamson. Nitrogen Nutrition of Containerized Citrus Nursery Plants. 1994. J. Amer. Soc. Hort. Sci., 119:195-201.
I.C. Oliveira et al. Overexpression of Cytosolic Glutamine Synthetase. Relation to Nitrogen, Light, and Photorespiration. 2002. Plant Physiol. 129:1170-1180.
I. Rajcan, M. Tollenaar. Source:sink ratio and leaf senescence in maize: II. Nitrogen metabolism during grain filling. 1999. Field Crops Res. 60:255-265.
S. Schiltz et al. Proteome Reference Maps of Vegetative Tissues in Pea. An Investigation of N Mobilization from Leaves during Seed Filling. 2004. Plant Physiol. 135:2241-2260.
S. Schiltz et al. Dynamics of Exogenous N Partitioning and N Remobilization from Vegetative Organs in Pea Revealed by 15N in vivo labeling.. 2005. Plant Physiol. 137:1463-1473.
R.H. Socolow. Nitrogen management and the future of food: Lessons from the management of energy and carbon. 1999. Proc. Natl. Acad. Sci. USA 96:6001-6008.
G. Xu, X. Fan, A.J. Miller. Plant Nitrogen Assimilation and Use Efficiency. 2012. Annu. Rev. Plant Biol. 63:153-182.

* cited by examiner

*Primary Examiner* — Matthew R Keogh

(57) ABSTRACT

This disclosure provides transgenic plants, including crop plants and methods for their production. The transgenic plants comprise recombinant DNA constructs for the expression of polypeptides encoded by the DNA constructs. The polypeptides are capable of conferring improved traits to the transgenic plants when expressed under the control of a tissue-enhanced promoter. This disclosure also pertains to transgenic plants and their progeny plants, wherein the transgenic or progeny plants comprise the recombinant DNA constructs and are selected for having enhanced nitrogen use efficiency and/or nitrogen uptake. Seed of the transgenic plants that can be grown into a plant that comprise the disclosed recombinant DNA constructs and exhibits having enhanced nitrogen use efficiency, and which may be selected for this trait, are also envisioned.

4 Claims, No Drawings

NITROGEN UPTAKE IN PLANTS

FIELD OF THE INVENTION

The present description relates to compositions and methods for improving nitrogen use efficiency in plants, for example, by improving nitrogen uptake or assimilation efficiency.

BACKGROUND

Nitrogen is a critical limiting nutrient for plants. Nitrogen fertilizer is a significant contributor to the yield increases obtained in the last several decades. However, these yield benefits have monetary and environmental costs, and nitrogen-based fertilizer represents a significant fraction of a farmer's input costs. Furthermore, crops only use a fraction of applied nitrogen. For example, it has been estimated that 50-70% of the nitrogen provided to the soil is lost (Masclaux-Daubresse et al., 2010, *Ann. Bot.* 105: 1141-1157; Hodge et al., 2000, *Trends Plant Sci.* 5: 304-308). Maize production in the US is reported to have a nitrogen fertilizer recovery efficiency of 37% (Cassman et al., 2002, *Ambio* 31: 132-140), and increased fertilizer application rates are subject to diminishing returns. A hectare of corn, for example, retains 39% of the first 100 kilograms of nitrogen applied as fertilizer, but only 13% of the second 100 kilograms of nitrogen applied (Socolow, 1999, *Proc. Natl. Acad. Sci. USA* 96: 6001-6008). As a consequence, nitrogen fertilizer that is not taken up by plants is generally lost as runoff or converted to nitrogen gases by microbial action, contributing to water and air pollution.

Thus, improving their efficiency of a crop plant's nitrogen use (i.e., its Nitrogen Use Efficiency, or N Use Efficiency, or NUE) would have the benefit of improving yield and agricultural sustainability while reducing negative environmental impact. NUE has been defined as increased grain yield per unit nitrogen available from the soil (Masclaux-Daubresse et al., 2010, supra), and thus it is judicious to identify means to increase the grain yield that may be obtained per unit nitrogen available from the soil.

Plants obtain nitrogen through the processes of uptake and assimilation (Buchanan et al., 2000, *Biochemistry and Molecular Biology of Plants*, American Society of Plant Physiologists, Rockville, Md.; Masclaux-Daubresse et al., 2010, supra). Uptake refers to the transport of nitrogen into the plant, and assimilation is the conversion of nitrate and ammonia to amino acids. Plants generally take up nitrogen from the soil in the form of nitrate or ammonium. Plants contain both low affinity and high affinity transport systems for these ions. In the case of nitrate, there is both a constitutive and an inducible high affinity transport system (Glass et al., 2002, *J. Exp. Bot.* 53: 855-864). Once nitrate crosses the plasma membrane, it is either metabolized in the cytoplasm of root cells or transported to the shoot via the xylem. For example, in wheat, up to 80% of the absorbed nitrate is reduced within the leaves (Ashley et al., 1975, *Plant Physiol.* 55: 1102-1106). Nitrate is reduced to ammonia through the action of nitrate reductase and nitrite reductase. Assimilation of ammonia takes place through the glutamine synthetase/glutamine-2-oxoglutarate aminotransferase (GS/GOGAT) pathway. Glutamine synthetase (GS) adds an amino group to glutamate to make glutamine, and GOGAT transfers the amino group to α-ketoglutarate to make a second molecule of glutamate. Photosynthesis provides the fixed carbon, energy, and reductant necessary for assimilation.

Plant nitrogen use efficiency could conceivably be increased by several mechanisms (Lawlor 2002, *J. Exp. Bot.* 53: 773-787). One mechanism could be increasing nitrogen uptake (which can be defined as the percentage of applied nitrogen taken up by plants (Maust and Williamson, 1994, *J. Amer. Soc. Hort. Sci.*, 119: 195-201), through higher root surface area, deeper penetration into the soil, or more high affinity nitrate or ammonium transporters. A second mechanism could be increased assimilation, possibly by increased activity of assimilatory enzymes or removal of negative regulation. Nitrogen utilization or assimilation efficiency, NUtE, is the fraction of plant-acquired nitrogen to be converted to total plant biomass or grain yield; (Xu et al., 2012, *Annu. Rev. Plant Biol.* 63:153-182). A third mechanism could be increased capacity to store nitrogen when it is available. Nitrogen is stored in the form of nitrate in cell vacuoles, but stored nitrate supplies are exhausted in a matter of days (Glass et al., 2002, supra). Nitrogen is also stored in the form of amino acids and protein, and this storage is dependent upon sufficient carbon availability. Control of nitrogen losses is also possible. Nitrate and ammonia exit as well as enter root cells. Photorespiration is another source of ammonia loss Ammonia released through photorespiration is recycled through the GS/GOGAT pathway, but this process may not be fully efficient. Overexpression of cytosolic glutamine synthetase in tobacco increased biomass produced, presumably through increased efficiency of ammonia recycling (Oliveira et al., 2002, *Plant Physiol.* 129: 1170-1180). The intrinsic nitrogen use efficiency (defined as biomass produced per unit N) could be changed by changing the plant's fundamental carbon/nitrogen ratio. Improving the NUE of crop plants has the potential to reduce fertilizer application rates, providing both cost savings and environmental benefits.

In spite of the apparent advantages of improved NUE, decades of research have not produced significant improvements in NUE in crops, and improved NUE is largely an unmet need in agriculture today.

The present description relates to methods and compositions for producing transgenic plants with modified traits, particularly traits that address agricultural and food needs by improving nitrogen use efficiency. In addition to reducing the demand for nitrogen application, it is expected that improving nitrogen use efficiency will improve yield and may provide significant value by allowing the plant to thrive in hostile environments, where, for example, low nutrient availability may limit yield or diminish or prevent growth of non-transgenic plants.

In this description, the expression levels of certain polynucleotide and polypeptide sequences identified herein may be manipulated to produce improved yield in commercially valuable plants and crops as well. Other aspects and embodiments of the description are described below and can be derived from the teachings of this disclosure as a whole.

SUMMARY OF THE DISCLOSURE

The present disclosure is directed to a method for producing a plant that has improved or enhanced nitrogen uptake and/or assimilation in the plant or in a part of the plant (for example, in roots or leaves;) relative to a control plant or its corresponding or analogous part. In this method, a plant is grown in a medium that contains either a limiting concentration of nitrogen that limits growth of the plant (for example, 2 mM total nitrogen in the medium) or an ample concentration of nitrogen that does not limit growth of the plant (for example, 10 mM total nitrogen in the medium).

Expression analysis of the plant may then reveal the presence of one or more polypeptides (the "instant polypeptides") that have a higher level of expression when the plant is grown in the limiting nitrogen medium as compared to plants grown in the medium with ample nitrogen. Genes may also be identified that, when overexpressed, produce changes in growth (e.g. enhanced root growth) or appearance (e.g. darker green leaves) in plate based assays using media with altered nitrogen or carbon content, or increased growth, biomass, nitrogen content, or photosynthetic capacity in soil-grown plants, and tested for the ability to confer enhanced nitrogen uptake and/or assimilation. The expression of a polypeptide identified in this manner may be regulated by a developmentally-regulated promoter. For example, expression of the promoter may be enhanced in root, root cap, root meristem, root vasculature, vascular, and/or green tissue; that is, the activity of the promoter is enhanced in one or more of these tissues relative to other plant tissues). It is anticipated that transformed plants that comprise one or more nucleic acid constructs that contain the tissue-enhanced promoter and a polynucleotide that encodes one of the instant polynucleotide will have greater nitrogen uptake and/or assimilation, as measured by such parameters as Nitrogen Uptake Efficiency (NUpE) or Usage Index (UI) relative to a control plant and as a result of the expression of the polynucleotide. The one or more nucleic acid constructs may be introduced into the plant by, for example, transformation or breeding. In this method, a regulator of gene expression may be identified that can enhance nitrogen uptake when expression of the regulator is enhanced in root, root cap, root meristem, root vasculature, vascular, and/or green tissue of the plant or a part of the plant. In this method, a transformed plant may be selected that has greater nitrogen uptake than the control plant.

The converse observation, in which expression analysis of the plant identifies one or more endogenous polypeptides that have a higher level of expression when the plant is grown in the ample nitrogen medium as compared to plants grown in the medium with limiting nitrogen, may be used to identify one or more endogenous polypeptides that may enhance nitrogen uptake and/or assimilation when expression of the endogenous polypeptide(s) is/are down-regulated. Down-regulation of expression may be accomplished with a means that suppresses transcription or translation of the endogenous polypeptide. Of some interest are suppressors of gene expression such as, for example, an RNAi molecule, an siRNA molecule, an antisense molecule, a ribozyme molecule, a deoxyribosyme molecule (a "DNAzyme") or a triple helix molecule that decreases the expression of the endogenous polypeptide. Gene expression suppressors may be introduced into a plant by breeding plants with a parental line that contains an instant gene expression suppressor, or by direct application or, in a desirable embodiment, by way of a nucleic acid construct that encodes the suppressor. It is anticipated that plants that comprise nucleic acid constructs encoding one or more of the instant suppressors will suppress or inhibit the activity of an instant polypeptide in the plant and thereby enhance nitrogen uptake in the plant. In this manner, a regulator of gene expression that can suppress protein expression or protein activity of the plant or a part of the plant may be identified.

The instant disclosure is also directed to a method for enhancing nitrogen uptake in a crop plant relative to a control plant by providing a transformed crop plant that comprises at least one of the instant recombinant nucleic acid constructs, and the construct or constructs comprise a tissue enhanced promoter that preferentially drives expression in root, root cap, root meristem, root vasculature, vascular, and/or green tissue, and in the same construct or a separate construct, an operably-linked polynucleotide the expression of which is regulated by the promoter. In this context, "providing" may refer to, for example, any one of the art-recognized means to introduce a nucleic acid construct into a plant or plant cell, such as by transformation or breeding where at least one parent line comprises at least one of the instant nucleic acid constructs (two parental lines may each contain an instant nucleic acid construct, as in the case when one plant line comprises a tissue-enhanced promoter that regulates expression of a polynucleotide comprised within a second promoter comprised within a different parental plant line). The polynucleotide encodes a polypeptide that is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131, or alternatively expressed as any of SEQ ID NOs: 2, 4, 6, 8, or any even integer to 2262. The tissue-enhanced promoter preferentially enhances expression of the polynucleotide in root, root cap, root meristem, root vasculature, vascular, and/or green tissue in the transformed plant or in a part of the transformed plant, and the preferential enhancement of expression results in increased nitrogen uptake in the transformed plant relative to the control plant.

Another aspect of the instant disclosure is a method of producing a crop plant with enhanced nitrogen uptake by providing a crop plant that has a stably-integrated, recombinant DNA construct comprising a promoter that is functional in plant cells and operably linked to DNA that encodes or suppresses a polypeptide presented in the Sequence Listing, or any of SEQ ID NOs: 2n, where n=1 to 1131, wherein the expression and activity of the polypeptide confers enhanced nitrogen uptake relative to a control plant. The methods further comprise producing seed and a progeny plant from the crop plant with enhanced nitrogen uptake, wherein the seed or progeny plant comprise the stably-integrated, recombinant DNA construct and the progeny plant or a plant grown from the seed exhibit enhanced nitrogen uptake relative to a control plant.

The instant disclosure also pertains to a recombinant nucleic acid construct comprising a root, root cap, root meristem, root vasculature, vascular, and/or green tissue-enhanced promoter that regulates expression of a polynucleotide, wherein the polynucleotide encodes a polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to any of SEQ ID NOs: 2, 4, 6, 8, or any even integer to 2262.

The instant disclosure also pertains to a transformed crop plant produced by any of the above described, methods, wherein the crop plant has enhanced nitrogen uptake relative to a control plant when the expression of an introduced or endogenous polypeptide provided in the sequence listing is enhanced or inhibited, respectively.

BRIEF DESCRIPTION OF THE SEQUENCE LISTING

The Sequence Listing provides exemplary polynucleotide and polypeptide sequences of the instant description. The traits associated with the use of the sequences are included in the Examples.

Incorporation of the Sequence Listing.

The Sequence Listing provides exemplary polynucleotide and polypeptide sequences. The copy of the Sequence Listing, being submitted electronically with this patent application, provided under 37 CFR § 1.821-1.825, is a read-only memory computer-readable file in ASCII text format. The Sequence Listing is named "MPS-0231P_ST25.txt," the electronic file of the Sequence Listing was created on Mar. 5, 2014, and is 8,181,555 bytes in size (7.80 megabytes in size as measured in MS-WINDOWS). The Sequence Listing is herein incorporated by reference in its entirety.

DETAILED DESCRIPTION

The present description relates to polynucleotides and polypeptides for modifying phenotypes of plants, particularly those associated with increased photosynthetic resource use efficiency and increased yield with respect to a control plant (for example, a wild-type plant). Throughout this disclosure, various information sources are referred to and/or are specifically incorporated. The information sources include scientific journal articles, patent documents, textbooks, and internet entries. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the instant description.

As used herein and in the appended claims, the singular forms "a", "an", and "the" include the plural reference unless the context clearly dictates otherwise. Thus, for example, a reference to "a host cell" includes a plurality of such host cells, and a reference to "a plant" is a reference to one or more plants, and so forth.

Definitions

"Upregulation" or "up-regulation" refers to a process in which a cell or an organism (e.g., a plant) increases the quantity of a cellular component, such as RNA or protein, in response to an internal or external signal. Upregulation may result in a greater activity of interest occurring in the cell or organism, for example, an increase in nitrogen uptake. Conversely, "downregulation" or "down-regulation" refers to a process by which a cell decreases the quantity of a cellular component, such as RNA or protein, in response to an internal or external signal. An internal or external signal may refer to, for example, an environmental variable such as a particular stress or a developmental marker such as molecule that signals the onset or occurrence of germination, root establishment, seedling growth, leaf production and canopy development, leaf senescence, reproduction (fertilization and seed development) or an environmental stress such as low environmental nitrogen, phosphorus, sulfur, iron, or potassium, salt stress, water stress, heat stress.

Tissue-specific, tissue-enhanced (that is, tissue-preferred), cell type-specific, and inducible promoters constitute non-constitutive promoters. Promoters under developmental control include promoters that preferentially initiate transcription in certain tissues, such as xylem, leaves, roots, or seeds. Such promoters are examples of tissue-enhanced or tissue-preferred promoters (see U.S. Pat. No. 7,365,186). Tissue-enhanced promoters can be found upstream and operatively linked to DNA sequences normally transcribed in higher levels in certain plant tissues or specifically in certain plant tissues, respectively. "Cell-enhanced", "tissue-enhanced", or "tissue-specific" regulation thus refer to the control of gene or protein expression, for example, by a promoter, which drives expression that is not necessarily totally restricted to a single type of cell or tissue, but where expression is elevated in particular cells or tissues to a greater extent than in other cells or tissues within the organism, and in the case of tissue-specific regulation, in a manner that is primarily elevated in a specific tissue. Tissue-enhanced or preferred promoters have been described in, for example, U.S. Pat. No. 7,365,186, U.S. Pat. No. 7,619,133, and by Noh and Amasino, 1999. *Plant Molec. Biol.* 41:181-194. Generally, root-specific, root cap-specific, root meristem-specific, root vasculature-specific, vascular-specific, and/or green tissue-specific promoters are transcriptionally active entirely or almost entirely in root, root cap, root meristem, root vasculature, vascular, and green tissue, respectively. Root-preferred or -enhanced, root cap-preferred or -enhanced, root meristem-preferred or -enhanced, root vasculature-preferred or -enhanced, vascular-preferred or -enhanced, and green tissue-preferred or -enhanced promoters are transcriptionally active predominantly in one or more of these tissues, but are not necessarily expressed only in these tissue. A root-specific, enhanced or preferred promoter may be preferentially active during root development and/or during germination. Examples of tissue-enhanced promoters are found in the present Sequence Listing, in Table 3, or have been taught in, for example, US patent publication U520130305414 or by Qing Qu and Takaiwa, 2004. *Plant Biotechnol. J.* 2:113-125).

An "inducible promoter" initiates transcription in response to an environmental stimulus such as a an external physical stimulus, for example, abiotic stimuli including energy or a particular chemical or class of chemicals, or a biotic stimulus, for example, a pathogen, or an internal stimulus such as one or more markers that signal a stage of development. Examples include "pathogen-inducible" promoters that initiate transcription in response to the presence of various pathogenic organisms or their products, and developmentally-induced promoters that are activated when a plant or plant part is at a particular growth stage, for example, "senescence-enhanced" (also referred to as "senescence-inducible") promoters. Senescence-enhanced promoters are active late in the life cycle of a plant during or near the time of senescence (Noh and Amasino, 1999. supra), and preferentially regulate expression of one or more genes (and any encoded polypeptides) during senescence of a plant cell from a leaf, flower, fruit, or other organ or plant part with respect to the level of expression of that gene in a non-senescing, i.e., a growing or mature (but pre-senescent) cell.

In the instant description, "endogenous" refers to a molecule that naturally originates from within a plant, plant tissue, or plant cell. The term "endogenous polypeptide" refers to a natural or native polypeptide that is encoded by a plant's native gene and thus it originates from within the plant, plant tissue, or plant cell upon its translation.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acids. An expression vector or cassette is an example of a "recombinant nucleic acid construct".

A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Conserved domains" are recurring units in molecular evolution, the extents of which can be determined by sequence and structure analysis. A "conserved domain" or "conserved region" as used herein refers to a region in heterologous polynucleotide or polypeptide sequences where there is a relatively high degree of sequence identity between the distinct sequences. Conserved domains contain conserved sequence patterns or motifs that allow for their detection in, and identification and characterization of, polypeptide sequences. A DNA-binding domain is an example of a conserved domain.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar or identical, or any integer value between 0-100%. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences. The fraction or percentage of components in common is related to the homology or identity between the sequences. An alignment may suitably be determined by means of computer programs known in the art, such as MACVECTOR software, 1999 (Accelrys®, Inc., San Diego, Calif.).

"Nitrogen use efficiency (NUE)" refers to the amount of nitrogen used to produce biomass or grain produced by a plant. Several methods have been developed to estimate NUE. Depending on the plant, either biomass or grain yield is measured. Likewise, estimates of the nitrogen used by the plant include determination of the amount of nitrogen taken up into the plant from soil or the nitrogen content of the plant.

Uptake" refers to the acquisition of nitrogen (in the form of nitrate, ammonium, or amino acids) from the soil by plant roots in plants. Generally, plants adapted to low pH and reducing soils as found in mature forests or arctic tundra tend to take up ammonium or amino acids, whereas plants adapted to higher pH and more aerobic soils prefer nitrate (Maathuis, 2009, *Curr. Opin. Plant Biol.* 12:250-258). Uptake occurs at the root level primarily (although some uptake can occur on the leaf surface in the case of atmospheric deposition) and specific transport systems exist for nitrate, ammonium, and amino acids.

"Assimilation" refers to the reduction of nitrate to ammonium, followed by ammonium assimilation into amino acids. Nitrate reduction to nitrite takes place in both roots and shoots but is spatially separated between the cytoplasm where the reduction takes place and plastids where nitrite reduction to ammonium occurs Ammonium (from nitrate reduction, photorespiration or amino acid recycling) is assimilated into amino acids via GS/GOGAT cycle. Glutamine synthetase (GS) fixes ammonium with glutamate to form glutamine. This glutamine reacts subsequently with 2-oxoglutarate to form two molecules of glutamate catalyzed by the glutamine 2-oxoglutarate amino transferase (or glutamate synthase, GOGAT).

"Usage index (UI)" refers to an estimate of nitrogen use efficiency (NUE). In measuring NUE, several definitions and evaluation methods have been developed (Good et al., (2004) *Trends Plant Sci.* 9:597-605). The "usage index" factors the absolute amount of biomass produced as well as for the ratio of biomass per unit nitrogen (tissue dry weight/nitrogen content). A plant is considered to have a higher usage index when the same amount of biomass is produced with less nitrogen or when more biomass is produced with the same amount of nitrogen compared to control plants.

"Nitrogen uptake efficiency (NupE)" is the ability of the plant to extract nitrogen from soil and fertilizer.

"Limiting nitrogen" refers to growth conditions which include a level (e.g., concentration) of nitrogen is applied which is below the level needed for normal plant metabolism, growth, reproduction and/or viability. Conversely, "ample nitrogen" refers to growth conditions which include a level (e.g., concentration) of nitrogen is applied which in excess of the level needed for normal plant metabolism, growth, reproduction and/or viability.

A "transgenic plant" or "transformed plant" refers to a plant that contains genetic material not found in a wild-type plant of the same species, variety or cultivar. The genetic material may include an expression vector or cassette, a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic line or transgenic plant line refers to the progeny plant or plants deriving from the stable integration of heterologous genetic material into a specific location or locations within the genome of the original transformed cell.

An expression vector or cassette typically comprises a polypeptide-encoding sequence operably linked (i.e., under regulatory control of) to appropriate inducible, tissue-enhanced, tissue-specific, developmentally-enhanced, or constitutive regulatory sequences that allow for the controlled expression of the polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

It is anticipated that a transgenic or transformed plant of the instant disclosure may have enhanced or greater nitrogen uptake relative to a control plant when the transgenic plant is transformed with a recombinant polynucleotide encoding any of the listed sequences, or when the transgenic plant contains or expresses a listed polypeptide, and as a consequence of the expression of the listed polypeptide within the transgenic or transformed plant.

A "seed-bearing structure", as used herein, refers to a plant part that comprises a developing or mature seed, and may include, but is not limited to, an achene, berry, capsule, caryopsis or grain, circumcissile capsule, cypsela, drupe, ear, fruit or ripened pericarp, follicle, grain, kernel, legume, loculicidal capsule, lomentum, nut, pistil, pod, poricidal capsule, samara, schizocarp, seed capsule, septicidal capsule, septifragal capsule, silicula, siliqua, silique or strobilus.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more transcription factors are under the control of a strong expression signal, such as one of the promoters described herein (for example, the cauliflower mosaic virus 35S transcription initiation region). Overexpression may occur throughout a plant or in specific tissues of the plant, depending on the promoter used, as described below.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

A "control plant" as used in the present disclosure refers to a plant such as a cell, seed, plant component, plant tissue, plant organ or whole plant used to compare against an altered or experimental plant such as a transgenic or genetically modified plant for the purpose of identifying an enhanced phenotype in the altered or experimental plant. A control plant may in some cases be a transgenic plant line that comprises an empty vector or marker gene, but does not contain the recombinant polynucleotide of the present description that is expressed in the transgenic or genetically modified plant being evaluated. In general, a control plant is a plant of the same line or variety as the experimental or altered plant being tested. A suitable control plant would include a genetically unaltered or non-transgenic plant of the parental line used to generate a transgenic plant herein.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A seed-bearing structure or organ refers to a organ of a plant that comprises a seed such as, for example, achene, berry, capsule, caryopsis or grain, circumcissile capsule, cypsela, drupe, ear, fruit or ripened pericarp, follicle, grain, kernel, legume, loculicidal capsule, lomentum, nut, pistil, pod, poricidal capsule, samara, schizocarp, seed capsule, septicidal capsule, septifragal capsule, silicula, siliqua, silique, strobilus, etc.

The term "overexpression" as used herein refers to a greater expression level of a gene in a plant, plant cell or plant tissue, compared to expression of that gene in a wild-type plant, cell or tissue, at any developmental or temporal stage. Overexpression can occur when, for example, the genes encoding one or more polypeptides are under the control of a strong promoter (e.g., the cauliflower mosaic virus 35S transcription initiation region). Overexpression may also be achieved by placing a gene of interest under the control of an inducible or tissue enhanced promoter, or may be achieved through integration of transposons or engineered T-DNA molecules into regulatory regions of a target gene. Other means for inducing overexpression may include making targeted changes in a gene's native promoter, e.g. through elimination of negative regulatory sequences or engineering positive regulatory sequences, though the use of targeted nuclease activity (such as zinc finger nucleases or TAL effector nucleases) for genome editing. Elimination of micro-RNA binding sites in a gene's transcript may also result in overexpression of that gene. Additionally, a gene may be overexpressed by creating an artificial transcriptional activator targeted to bind specifically to its promoter sequences, comprising an engineered sequence-specific DNA binding domain such as a zinc finger protein or TAL effector protein fused to a transcriptional activation domain. Thus, overexpression may occur throughout a plant, in specific tissues of the plant, or in the presence or absence of particular environmental signals, depending on the promoter or overexpression approach used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

"Yield" or "plant yield" refers to increased plant growth, increased crop growth, increased biomass, and/or increased plant product production (including grain), and is dependent to some extent on temperature, plant size, organ size, planting density, light, water and nutrient availability, and how the plant copes with various stresses, such as through temperature acclimation and water or nutrient use efficiency. Increased or improved yield may be measured as increased seed yield, increased plant product yield (plant products include, for example, plant tissue, including ground or otherwise broken-up plant tissue, and products derived from one or more types of plant tissue), or increased vegetative yield.

DESCRIPTION OF THE SPECIFIC EMBODIMENTS

Improving a plant's ability to take up and utilize nitrogen from the soil is an important agronomic goal. Two important measures of this ability are the nitrogen uptake efficiency (NUpE), defined as the amount of nitrogen taken up per unit of plant biomass, and the Usage Index (UI), defined as plant biomass/% nitrogen. Usage index is accepted as a measurement of nitrogen use efficiency (NUE) for vegetative stage plants. NUpE and UI are controlled both by genetic and environmental factors. Genetic variability in these parameters exists among crop plants. However, genetically identical plants grown on limiting nitrogen have higher NUpE than plants grown under ample nitrogen. Improving NUpE and UI either in limiting or ample nitrogen conditions is expected to improve crop yield. Potential strategies to improve UI or NUpE with the instantly listed sequences or other clade member sequences include increased expression of regulators (or effectors) of nitrogen uptake in roots, leaves, or whole plants.

Polypeptides and Polynucleotides of the Present Description.

The present description includes increased or ectopic expression of putative regulatory polypeptides (i.e., regulators or effectors of nitrogen uptake) and isolated or recombinant polynucleotides encoding the polypeptides, or novel sequence variant polypeptides or polynucleotides encoding novel variants of polypeptides derived from the specific sequences provided in the Sequence Listing. The polynucleotides of the instant description may be incorporated in expression vectors for the purpose of producing transformed plants.

Because of their relatedness at the nucleotide level, the claimed sequences will typically share at least about 40% nucleotide sequence identity, or at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or at least 96%, at least 97%, at least 98%, at least 99%, or about 100% sequence identity to one or more of the listed sequences or to the full-length listed sequences (e.g., any of SEQ ID NO: 2n–1, where n=1 to 1131), or to a listed sequence within or outside of the region(s) encoding a known consensus sequence or consensus DNA-binding site, or to a listed conserved domain sequence, or within or outside of the region(s) encoding one or all conserved domains. The degeneracy of the genetic code enables major variations in the nucleotide sequence of a polynucleotide while maintaining the amino acid sequence of the encoded protein.

Because of their relatedness at the protein level, the claimed nucleotide sequences will typically encode a polypeptide that is at least at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical in its amino acid sequence to any of, or the entire length of any of, SEQ ID NOs: 2n, where n=1 to 1131, or 2, 4, 6, 8, or any even integer to 2262.

Also provided are methods for modifying yield from a plant by enhancing the nitrogen use efficiency or a plant's nitrogen uptake of a plant by controlling a number of cellular processes by, for example, introducing into a target plant a gene that encodes a polypeptide that confers enhanced nitrogen uptake. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased yield or photosynthetic resource use efficiency in diverse plant species.

Sequences in the Sequence Listing, derived from diverse plant species, may be ectopically expressed in overexpressor plants. The changes in the characteristic(s) or trait(s) of the plants may then be observed and found to confer increased yield and/or increased nitrogen use efficiency and/or nitrogen uptake. Therefore, the polynucleotides and polypeptides can be used to improve desirable characteristics of plants.

The polynucleotides of the instant description are also ectopically expressed in overexpressor plant cells and the changes in the expression levels of a number of genes, polynucleotides, and/or proteins of the plant cells observed. Therefore, the polynucleotides and polypeptides can be used to change expression levels of genes, polynucleotides, and/or proteins of plants or plant cells.

The data presented herein represent the results obtained in experiments with polynucleotides and polypeptides that may be expressed in plants for the purpose of increasing yield that arises from improved nitrogen use efficiency and/or nitrogen uptake.

The polynucleotides and polypeptides of the instant description, that, when expressed in plants or crop plant have the capacity to enhance nitrogen uptake in a plant or a part of a plant relative to a control plant or a corresponding part of the control plant, include:

SEQ ID NOs:1 and 2, AT2G24570.1 (G866) and clade member sequences SEQ ID NOs:3-74;

SEQ ID NOs:75 and 76, AT2G37430.1 (G355) and clade member sequences SEQ ID NOs:77-134;

SEQ ID NOs:1 and 136, AT1G07900.1 (G4083) and clade member sequences SEQ ID NOs:137-198;

SEQ ID NOs:199 and 200, AT1G74080.1 (G2340) and clade member sequences SEQ ID NOs:201-204;

SEQ ID NOs:205 and 206, AT1G62300.1 (G184) and clade member sequences SEQ ID NOs:207-286;

SEQ ID NOs:287 and 288, AT1G18860.1 (G2110) and clade member sequences SEQ ID NOs:289-358;

SEQ ID NOs:359 and 360, AT3G23250.1 (G233) and clade member sequences SEQ ID NOs:361-426;

SEQ ID NOs:427 and 428, AT2G26150.1 (G266) and clade member sequences SEQ ID NOs:429-456;

SEQ ID NOs:457 and 458, AT3G15500.1 (G773) and clade member sequences SEQ ID NOs:459-490;

SEQ ID NOs:491 and 492, AT1G16150.1 and clade member sequences SEQ ID NOs:493-538;

SEQ ID NOs:539 and 540, AT1G51800.1 and clade member sequences SEQ ID NOs:541-758;

SEQ ID NOs:759 and 760, AT1G61440.1 and clade member sequences SEQ ID NOs:761-950;

SEQ ID NOs:951 and 952, AT4G11470.1, SEQ ID NOs: 953 and 954, and AT4G11480.1 and clade member sequences SEQ ID NOs:955-1212;

SEQ ID NOs:1213 and 1214, AT5G14640.1 and clade member sequences SEQ ID NOs: 1215-1374;

SEQ ID NOs:1375 and 1376, AT5G06740.1 and clade member sequences SEQ ID NOs: 1377-1400;

SEQ ID NOs:1401 and 1402, AT2G19190.1 and clade member sequences SEQ ID NOs:1403-1672;

SEQ ID NOs:1673 and 1674, AT1G57560.1 (G1319) and clade member sequences SEQ ID NOs: 1675-1752;

SEQ ID NOs:1753 and 1754, AT2G46510.1 (G1665) and clade member sequences SEQ ID NOs: 1755-1786;

SEQ ID NOs:1787 and 1788, AT5G54900.1 (G1940) and clade member sequences SEQ ID NOs: 1789-1920;

SEQ ID NOs:1921 and 1922, AT3G05200.1 (G2239) and clade member sequences SEQ ID NOs: 1923-2026;

SEQ ID NOs:2027 and 2028, AT2G34450.2 (G2898) and clade member sequences SEQ ID NOs:2029-2054;

SEQ ID NOs:2055 and 2056, AT5G26930.1 (G348) and clade member sequences SEQ ID NOs:2057-2090;

SEQ ID NOs:2091 and 2092, AT4G20380.1 (G347) and clade member sequences SEQ ID NOs:2093-2166;

SEQ ID NOs:2167 and 2168, AT1G09030.1 (G486) and clade member sequences SEQ ID NOs:2169-2242; and SEQ ID NOs:2243 and 2244, AT2G43260.1 (G1466) and clade member sequences SEQ ID NOs:2245-2262.

Variants of the Disclosed Sequences.

Also within the scope of the instant description is a variant of a nucleic acid provided in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity). The variant nucleic acid may, for example, encode the same polypeptide but differ in sequence from the sequence in the Sequence Listing due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in functionally equivalent polypeptides. Thus, it will be readily appreciated by those of skill in the art, that any of a variety of polynucleotide sequences is capable of encoding the polypeptides and homolog polypeptides of the instant description. A polypeptide sequence variant may have "conservative" changes, wherein a substituted amino acid has similar structural or chemical properties.

Conservative substitutions include substitutions in which at least one residue in the amino acid sequence has been removed and a different residue inserted in its place. Such substitutions generally are made in accordance with the Table 1 when it is desired to maintain the activity of the protein. Table 1 shows amino acids which can be substituted for an amino acid in a protein and which are typically regarded as conservative substitutions.

TABLE 1

Possible conservative amino acid substitutions

| Amino Acid Residue | Conservative substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Pro | Gly |
| Ser | Thr; Gly |
| Thr | Ser; Val |
| Trp | Tyr |
| Tyr | Trp; Phe |
| Val | Ile; Leu |

The polypeptides provided in the Sequence Listing have a novel activity, such as, for example, a regulatory activity. Although all conservative amino acid substitutions (for example, one basic amino acid substituted for another basic amino acid) in a polypeptide will not necessarily result in the polypeptide retaining its activity, it is expected that many of these conservative mutations would result in the polypeptide retaining its activity. Most mutations, conservative or non-conservative, made to a protein but outside of a conserved domain required for function and protein activity will not affect the activity of the protein to any great extent.

Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or 0-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840, 544).

Conserved Domains.

Conserved domains are recurring functional and/or structural units of a protein sequence within a protein family (for example, a family of regulatory proteins), and distinct conserved domains have been used as building blocks in molecular evolution and recombined in various arrangements to make proteins of different protein families with different functions. Conserved domains often correspond to the 3-dimensional domains of proteins and contain conserved sequence patterns or motifs, which allow for their detection in polypeptide sequences with, for example, the use of a Conserved Domain Database (for example, at www.ncbi.nlm.nih.gov/cdd). The National Center for Biotechnology Information Conserved Domain Database defines conserved domains as recurring units in molecular evolution, the extents of which can be determined by sequence and structure analysis. Conserved domains contain conserved sequence patterns or motifs, which allow for their detection in polypeptide sequences (Conserved Domain Database; www.ncbi.nlm.nih.gov/Structure/cdd/cdd.shtml). A "conserved domain" or "conserved region" as used herein refers to a region in heterologous polynucleotide or polypeptide sequences where there is a relatively high degree of sequence identity between the distinct sequences. A 'Myb DNA binding domain 1' is an example of a conserved domain.

Conserved domains may also be identified as regions or domains of identity to a specific consensus sequence (see, for example, Riechmann et al., 2000, *Science* 290, 2105-2110; Riechmann et al., 2000, *Curr Opin Plant Biol* 3: 423-434). Thus, by using alignment methods well known in the art, the conserved domains of the plant polypeptides, for example, for the first or second Myb DNA binding domain proteins may be determined. The polypeptides in Table 2 have conserved domains specifically indicated by amino acid coordinate start and stop sites. A comparison of the regions of these polypeptides allows one of skill in the art (see, for example, Reeves and Nissen, 1990. *J. Biol. Chem.* 265, 8573-8582; Reeves and Nissen, 1995. *Prog. Cell Cycle Res.* 1: 339-349) to identify domains or conserved domains for any of the polypeptides listed or referred to in this disclosure.

Conserved domain models are generally identified with multiple sequence alignments of related proteins spanning a variety of organisms. These alignments reveal sequence regions containing the same, or similar, patterns of amino acids. Multiple sequence alignments, three-dimensional structure and three-dimensional structure superposition of conserved domains can be used to infer sequence, structure, and functional relationships (Conserved Domain Database, supra). Since the presence of a particular conserved domain within a polypeptide is highly correlated with an evolutionarily conserved function, a conserved domain database may be used to identify the amino acids in a protein sequence that are putatively involved in functions such as binding or catalysis, as mapped from conserved domain annotations to the query sequence. For example, the presence in a protein of a DNA binding domain that is structurally and phylogenetically similar to one or more domains found in the sequence listing would be a strong indicator of a related function in plants (e.g., the function of regulating and/or improving nitrogen use efficiency, nitrogen uptake, and/or yield, i.e., a polypeptide with such a domain is expected to confer enhanced nitrogen use efficiency, nitrogen uptake, and/or yield when its expression level is increased under the regulatory control of a tissue-enhanced promoter). Sequences herein referred to as functionally-related and/or closely-related to the sequences or domains provided in the Sequence Listing, including polypeptides that are closely related to the polypeptides of the instant description, may have conserved domains that share at least at least nine base pairs (bp) in length and at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% amino acid sequence identity to the sequences provided in the Sequence Listing, and have similar functions in that the polypeptides of the instant description, where the presence of the listed or claimed domains in said polypeptides is positively correlated or associated with the function(s) of said polypeptides in plants. Said polypeptides may, when their expression level is altered and confer at least one regulatory activity selected from the group consisting of enhanced nitrogen uptake and/or assimilation, as measured by such parameters as Nitrogen Uptake Efficiency (NUpE) or Usage Index (UI), increased nitrogen use efficiency, greater yield, greater size, greater biomass, and/or greater vigor as compared to a control plant.

Methods using manual alignment of sequences similar or homologous to one or more polynucleotide sequences or one or more polypeptides encoded by the polynucleotide sequences may be used to identify regions of similarity and conserved domains (e.g., DNA binding domains, activation domains, localization domains, repression domains, oligomerization domains, or other domains that are recognizably related across plant species. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted α-helices, β-sheets, amphipathic helices, leucine zipper motifs, zinc finger motifs, proline-rich regions, cysteine repeat motifs, and the like.

With respect to polynucleotides encoding presently disclosed polypeptides, a conserved domain refers to a subsequence within a polypeptide family the presence of which is correlated with at least one function exhibited by members of the polypeptide family, and which exhibits a high degree of sequence homology, such as at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identity to a conserved domain (e.g., any of SEQ ID NOs: 2263-2312) of a polypeptide (e.g., any of SEQ ID NOs: 2n, where n=1 to 1131) of the Sequence Listing. Sequences that possess or encode for conserved domains that meet these criteria of percentage identity, and that have comparable biological and regulatory activity to the present polypeptide sequences. Sequences having lesser degrees of identity but comparable biological activity are considered to be equivalents.

Table 2 lists *Arabidopsis* sequence identifiers and the descriptions of various domains found within the respective proteins, including the domain names, the linear coordinates of the amino acids at the beginning and end of the respective domains, and the SEQ ID NOs: of the domains listed in this table. It is expected that domains of clade member polypeptides of each of these sequences, examples of said polypeptides being provided in the Sequence Listing, function similarly in plants and their presence is indicative of and correlated with the same functions as the domains in the *Arabidopsis* sequences.

TABLE 2

Various *Arabidopsis* domains found in polypeptide sequences that enhance nitrogen uptake in plants

| Sequence | Domain Name | Starting amino acid in protein sequence | Last amino acid in protein sequence | SEQ ID NO: of Domain |
|---|---|---|---|---|
| AT1G16150.1 | Wall-associated receptor kinase galacturonan-binding | 51 | 144 | 2263 |
| AT1G16150.1 | Wall-associated kinase | 174 | 279 | 2264 |
| AT1G16150.1 | protein kinase catalytic (PKc) domain | 442 | 708 | 2265 |
| AT1G57560.1 | Myb domain 1 (AKA SANT domain) | 14 | 61 | 2266 |
| AT1G57560.1 | Myb domain 2 (AKA SANT domain) | 67 | 112 | 2267 |
| AT1G09030.1 | CCAAT-binding transcription factor (NF-YB) | 6 | 71 | 2268 |
| AT1G51800.1 | Malectin-like | 32 | 353 | 2269 |
| AT1G51800.1 | Leucine rich repeat (LRR8) | 412 | 468 | 2270 |
| AT1G51800.1 | protein kinase catalytic (PKc) domain | 609 | 855 | 2271 |
| AT1G18860.1 | WRKY DNA binding domain | 191 | 248 | 2272 |
| AT1G61440.1 | Bulb-type mannose-specific lectin | 24 | 139 | 2273 |
| AT1G61440.1 | S-locus glycoprotein family | 198 | 305 | 2274 |
| AT1G61440.1 | PAN/APPLE-like domain | 322 | 407 | 2275 |
| AT1G61440.1 | Tyrosine kinase catalytic (TyrKc) domain | 479 | 741 | 2276 |
| AT1G07900.1 | Lateral organ boundaries (LOB) domain | 34 | 133 | 2277 |
| AT1G74080.1 | SANT (aka Myb) | 16 | 61 | 2278 |
| AT11G74080.1 | SANT (aka Myb) | 69 | 112 | 2279 |
| AT2G43260.1 | F-box-associated domain | 102 | 294 | 2280 |
| AT2G26150.1 | HSF DNA binding domain | 44 | 136 | 2281 |
| AT2G46510.1 | N-terminal domain associated with bHLH-MYC domain | 48 | 239 | 2282 |
| AT2G46510.1 | Helix-loop-helix domain (HLH) | 394 | 445 | 2283 |
| AT2G19190.1 | Malectin-like | 33 | 359 | 2284 |
| AT2G19190.1 | Leucine rich repeat (LRR8) | 415 | 474 | 2285 |
| AT2G19190.1 | protein kinase catalytic (PKc) domain | 580 | 766 | 2286 |
| AT2G37430.1 | C2H2-type zinc finger | 47 | 72 | 2287 |
| AT2G37430.1 | C2H2-type zinc finger | 93 | 118 | 2288 |
| AT2G24570.1 | Plant zinc cluster domain | 191 | 240 | 2289 |
| AT2G24570.1 | WRKY DNA-binding domain | 242 | 300 | 2290 |

TABLE 2-continued

Various *Arabidopsis* domains found in polypeptide sequences that enhance nitrogen uptake in plants

| Sequence | Domain Name | Starting amino acid in protein sequence | Last amino acid in protein sequence | SEQ ID NO: of Domain |
|---|---|---|---|---|
| AT2G34450.2 | High mobility group box | 63 | 129 | 2291 |
| AT3G05200.1 | C3HC4 RING finger | 125 | 171 | 2292 |
| AT3G23250.1 | SANT (aka Myb) | 16 | 61 | 2293 |
| AT3G23250.1 | SANT (aka Myb) | 69 | 112 | 2294 |
| AT3G15500.1 | NAM | 14 | 140 | 2295 |
| AT4G22070.1 | WRKY | 298 | 354 | 2296 |
| AT4G11470.1 | Salt stress response/antifungal | 23 | 130 | 2297 |
| AT4G11470.1 | Salt stress response/antifungal | 189 | 245 | 2298 |
| AT4G11470.1 | Tyrosine kinase catalytic (TyrKc) domain | 342 | 611 | 2299 |
| AT4G11480.1 | Salt stress response/antifungal | 23 | 126 | 2300 |
| AT4G11480.1 | Salt stress response/antifungal | 142 | 236 | 2301 |
| AT4G11480.1 | Protein kinase catalytic (PKc) domain | 325 | 602 | 2302 |
| AT4G20380.1 | LSD1 zinc finger | 4 | 34 | 2303 |
| AT4G20380.1 | LSD1 zinc finger | 45 | 75 | 2304 |
| AT4G20380.1 | LSD1 zinc finger | 95 | 119 | 2305 |
| AT5G54900.1 | RNA recognition motif 1 | 61 | 141 | 2306 |
| AT5G54900.1 | RNA recognition motif 2 | 153 | 232 | 2307 |
| AT5G54900.1 | RNA recognition motif 3 | 260 | 332 | 2308 |
| AT5G06740.1 | lectin domain | 25 | 257 | 2309 |
| AT5G06740.1 | Protein tyrosine kinase | 335 | 606 | 2310 |
| AT5G26930.1 | GATA zinc finger | 28 | 62 | 2311 |
| AT5G14640.1 | Protein kinase domain | 77 | 358 | 2312 |

Orthologs and Paralogs.

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen, 1998. *Genome Res.* 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al., 1994, *Nucleic Acids Res.* 22: 4673-4680; Higgins et al., 1996, *Methods Enzymol.* 266: 383-402). Groups of similar genes can also be identified with pair-wise BLAST analysis (Feng and Doolittle, 1987, *J. Mol. Evol.* 25: 351-360). For example, a clade of very similar MADS domain transcription factors from *Arabidopsis* all share a common function in flowering time (Ratcliffe et al., 2001, *Plant Physiol.* 126: 122-132), and a group of very similar AP2 domain transcription factors from *Arabidopsis* are involved in tolerance of plants to freezing (Gilmour et al., 1998, supra). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, 2001, in *Bioinformatics: Sequence and Genome Analysis*, Cold Spring Harbor Laboratory Press, Cold Spring Harbor, N.Y., p. 543)

Regulatory polypeptide gene sequences are conserved across diverse eukaryotic species lines (Goodrich et al., 1993. *Cell* 75:519-530; Lin et al., 1991, *Nature* 353:569-571; Sadowski et al., 1988, *Nature* 335: 563-564). Plants are no exception to this observation; diverse plant species possess regulatory polypeptides that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994, supra; Higgins et al., 1996, supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

The polypeptides sequences belong to distinct clades of polypeptides that include members from diverse species. In each case, most or all of the clade member sequences derived from both eudicots and monocots have been shown and are predicted to enhance nitrogen uptake to confer increased yield when the sequences were overexpressed under the regulatory control of, for example, a root, root cap, root meristem, root vasculature, vascular, and/or green tissue-enhanced promoter. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

Orthologs and paralogs of presently disclosed polypeptides may be cloned using compositions provided by the present description according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in the present Sequence Listing. In addition to the *Arabidopsis* polypeptide sequences in the Sequence Listing, these orthologs are phylogenetically and structurally similar to the sequences in the Sequence Listing and can also function in a plant by increasing nitrogen use efficiency, nitrogen uptake, yield, vigor, and/or biomass when ectopically and preferentially expressed in a plant or in a plant organ. Since a significant number of these sequences are phylogenetically and sequentially related to each other and may be shown to increase yield from a plant and/or nitrogen uptake, one skilled in the art would predict that other similar, phylogenetically related sequences, including those falling within the present clades of polypeptides or having the same consensus sequences or which are sequentially similar, having a disclosed minimum percentage identity to one another or the listed *Arabidopsis* polypeptide, would also perform similar functions when ectopically expressed under the regulatory control of the disclosed promoters or other root, root cap, root meristem, root vasculature, vascular, and/or green tissue-enhanced promoters.

Promoters.

The tissue-enhanced promoters in Table 3 preferentially regulate gene expression in root, root cap, root meristem, root vasculature, and/or vascular tissue structures or organs relative to other tissues in a plant. Examples of tissue-enhanced promoters may also be found in the Sequence Listing as SEQ ID NOs: 2313 to 2349.

The choice of promoter may also include a constitutive promoter or a promoter with enhanced activity in a tissue capable of photosynthesis (also referred to herein as a "green tissue promoter", a "photosynthetic promoter" or a "photosynthetic tissue-enhanced promoter") such as a leaf tissue or other green tissue. Examples of photosynthetic or green tissue promoters include for example, an RBCS3 promoter (SEQ ID NO: 2323), an RBCS4 promoter (SEQ ID NO: 2324) others such as the At4g01060 promoter (SEQ ID NO: 2325), the latter regulating expression in a guard cell, or rice sequences SEQ ID NOs: 2326 to 2349, shown in Table 3 or in the Sequence Listing.

TABLE 3

Exemplary promoters

| Promoter | SEQ ID NO | Organism from which promoter is derived | Tissue | Reference |
|---|---|---|---|---|
| Os03g01700 | 2350 | rice | root | Li et al., 2013. Plant Sci. 207:37-44 |
| Os02g37190 | 2351 | rice | root | Li et al., 2013. Plant Sci. 207:37-44 |
| rolD | 2352 | *Agrobacterium rhizogenes* | root | Leach and Aoyagi. 1991. Plant Sci. 79:69-76 |
| RCc3 | 2353 | rice | root | Xu et al. 1995. Plant Mol. Biol. 27:237-248 |
| TobRB7 | 2354 | tobacco | root | Yamamoto, et al. 1991. Plant Cell 3:371-382 |
| Pyk10 | 2355 | *Arabidopsis* | root | Nitz et al. 2001. Plant Sci. 161:337-346 |
| PmPR10-1.14 | | *Pinus monticola* | root | Liu and Ekramoddoullah. 2003. Plant Mol. Biol. 52:103-120 |
| HvPht1;1 | 2356 | barley | root | Schünmann et al. 2004. J. Exp. Bot. 55:855-865 |
| HvPht1;2 | 2357 | barley | root | Schünmann 2004. J. Exp. Bot. 55:855-865 |
| MsPRP2 | | alfalfa | root | Winicov et al. 2004. Planta 219:925-935 |

TABLE 3-continued

Exemplary promoters

| Promoter | SEQ ID NO | Organism from which promoter is derived | Tissue | Reference |
|---|---|---|---|---|
| PHT1 | 2358 | *Arabidopsis* | root | Koyama et al. 2005. J. Biosci. Bioeng. 99: 38-42 |
| At1g73160 | 2359 | *Arabidopsis* | root | Vijaybhaskar et al. 2008. J. Biosci. 33; 185-193 |
| AtCel5 | 2360 | *Arabidopsis* | root cap | del Campillo et al. 2004. Plant Mol. Biol. 56: 309-323 |
| ARSK1 | 2361 | *Arabidopsis* | root | Hwang and Goodman. 1995. Plant J. 8:37-43 |
| RSI1 | 2362 | tomato | root meristem and vasculature | Taylor and Scheuring 1994. Mol. Gen. Genet. 243:148-157 |
| AT2G39850 | 2313 | *Arabidopsis* | vascular | SEQ ID NO: 27 of US patent pub. US20110179520 |
| AT2G03500 | 2314 | *Arabidopsis* | vascular | SEQ ID NO: 22 US patent pub. US20110179520 |
| AT3G42670 | 2315 | *Arabidopsis* | vascular | SEQ ID NO: 34 US patent pub. US20110179520 |
| AT1G24735 | 2316 | *Arabidopsis* | vascular | SEQ ID NO: 5 US patent pub. U520110179520 |
| AT5G56530 | 2317 | *Arabidopsis* | vascular | SEQ ID NO: 63 US patent pub. US20110179520 |
| AT3G12750 | 2318 | *Arabidopsis* | vascular | SEQ ID NO: 29 US patent pub. U520110179520 |
| AT3G16340 | 2319 | *Arabidopsis* | vascular | SEQ ID NO: 31 US patent pub. US20110179520 |
| AT1G65150 | 2320 | *Arabidopsis* | vascular | SEQ ID NO: 16 US patent pub. U520110179520 |
| AT5G27690 | 2321 | *Arabidopsis* | vascular | SEQ ID NO: 58 US patent pub. U520110179520 |
| AT1G10155 | 2322 | *Arabidopsis* | vascular | SEQ ID NO: 2 US patent pub. U520110179520 |
| SUC2 | 2363 | *Arabidopsis* | vascular | Truernit and Sauer. 1995. Planta 196:564-570 |
| CoYMV |  | Commelina yellow mottle virus | vascular | Medberry et al. 1992. Plant Cell 4:185-192 |
| Sucrose synthase |  | Rice | vascular | Wang et al. 1992. Plant Mol. Biol. 19:881-885 |
| Sucrose synthase | 2364 | maize | vascular | Yang and Russell. 1980. Proc. Natl Acad. Sci. USA 87:4144-4148 |
| GmSBP2 | 2365 | Glycine max | vascular | Waclawovsky et al. 2006. BBA-Gene Struct. Expr. 1759:89-98 |
| Rplec2 | 2366 | *Robinia pseudoacacia* | vascular | Yoshida et al. 2002. J. Plant Physiol. 159:757-764 |
| PP2 |  | *Cucurbita maxima* | vascular | Jiang et al. 1999. J. Agric. Biotechnol. 7:63-68 |
| PP2 |  | *Cucurbita maxima* | vascular | Thompson and Larkins. 1996. US patent pub. U5005495007A |
| rolC | 2367 | *Agrobacterium rhizogenes* | vascular | Schmulling et al. 1989. Plant Cell 1:665-670 |
| RTBV |  | rice tungro bacilliform virus | vascular | Yin and Beachy. 1997. Plant J. 12:1179-1188 |
| DX1 (Os12g33120) | 2368 | rice | green tissue | Zhou and Lin. 2012. Plant Cell Rep. 31:1159-1172. doi:10.1007/s00299-012-1238-8 |
| RBCS3 | 2323 | tomato | green tissue | Wanner and Gruissem. 1991. Plant Cell 3: 1289-1303 |
| RBCS4/RBCS1A | 2324 | *Arabidopsis* | green tissue |  |
| PEPC | 2369 | maize | green tissue | Koziel et al. 1993. Nature Biotechnol. 11:194-200 |
| prG682 At4g01060 | 2325 | *Arabidopsis* | guard cell |  |
| Os02g09720 | 2326 | rice | green tissue |  |
| Os05g34510 | 2327 | rice | green tissue |  |
| Os11g08230 | 2328 | rice | green tissue |  |
| Os01g64390 | 2329 | rice | green tissue |  |
| Os06g15760 | 2330 | rice | green tissue |  |
| Os12g37560 | 2331 | rice | green tissue |  |
| Os03g17420 | 2332 | rice | green tissue |  |
| Os04g51000 | 2333 | rice | green tissue |  |
| Os01g01960 | 2334 | rice | green tissue |  |
| Os05g04990 | 2335 | rice | green tissue |  |
| Os02g44970 | 2336 | rice | green tissue |  |
| Os01g25530 | 2337 | rice | green tissue |  |

TABLE 3-continued

Exemplary promoters

| Promoter | SEQ ID NO | Organism from which promoter is derived | Tissue | Reference |
|---|---|---|---|---|
| Os03g30650 | 2338 | rice | green tissue | |
| Os01g64910 | 2339 | rice | green tissue | |
| Os07g26810 | 2340 | rice | green tissue | |
| Os07g26820 | 2341 | rice | green tissue | |
| Os09g11220 | 2342 | rice | green tissue | |
| Os04g21800 | 2343 | rice | green tissue | |
| Os10g23840 | 2344 | rice | green tissue | |
| Os08g13850 | 2345 | rice | green tissue | |
| Os12g42980 | 2346 | rice | green tissue | |
| Os03g29280 | 2347 | rice | green tissue | |
| Os03g20650 | 2348 | rice | green tissue | |
| Os06g43920 | 2349 | rice | green tissue | |
| psaDb | | tobacco | green tissue | Yamamoto et al. 1997. Plant J. 12:255-265 |
| gapb | 2370 | Arabidopsis | green tissue | Kwon et al. 1994. Plant Physiol. 105:357-367 |
| cab 1 | | wheat | green tissue | Gotor et al. 1993. Plant J. 3:509-518 |
| cab 6 | | pine | green tissue | Yamamoto et al. 1994. Plant Cell Physiol. 35:773-778 |
| rbcs activase | | spinach | green tissue | Orozco et al. 1993. Plant Mol. Biol. 23: 1129-1138 |
| ppdk | 2371 | maize | green tissue | Matsuoka et al. 1993. Proc. Natl. Acad. Sci. USA 90:9586-9590 |
| lhcb1 * 2 | 2372 | tobacco | green tissue | Cerdan et al. 1997. Plant Mol. Biol. 33:245-255 |

EXAMPLES

It is to be understood that this description is not limited to the particular devices, machines, materials and methods described. Although particular embodiments are described, equivalent embodiments may be used to practice the claims.

The specification, now being generally described, will be more readily understood by reference to the following examples, which are included merely for purposes of illustration of certain aspects and embodiments of the present description and are not intended to limit the claims or description. It will be recognized by one of skill in the art that a polypeptide that is associated with a particular first trait may also be associated with at least one other, unrelated and inherent second trait which was not predicted by the first trait.

Example I. Identification of Regulators of UI and NUpE Through Gene Expression Profiling Plants grown under limiting nitrogen conditions take up and utilize nitrogen more efficiently than do plants grown under ample nitrogen. To elucidate the regulatory networks controlling these differences, a transcriptional profiling experiment was performed on *Arabidopsis* plants grown under conditions of limiting (2 mM) and ample (10 mM) nitrogen. Leaf and silique tissue were harvested beginning in the vegetative phase and continuing through seed development to create a developmental time series under these two different nutrient regimes.

Plant Growth and Tissue Isolation.

Plants were grown in pots containing three volumes of fritted clay at bottom and one volume of fine sand on top. Pots were pre-soaked in nutrient solution containing either 2 mM (low N) or 10 mM (high N) nitrate solution. Phosphate (0.25 mM), sulfate (0.25 mM), magnesium (0.25 mM), and sodium (0.20 mM) were present in both solutions at the same concentration. The difference between low and high N solutions affects only potassium (5.25 mM and 2.75 mM in high and low N solutions, respectively), calcium (2.50 mM and 0.50 mM, respectively), and chloride ions (0.25 mM and 0.70 mM, respectively). Pots were placed in Conviron growth chambers at a day temperature of 22° C. (19° C. night) with a 16 hr photoperiod at an initial light intensity of ~100 µmol m−2 s−1 and a final light intensity of −140 µmol m−2 s−1 at plant height. After two weeks, flats were moved to a commercial ebb and flow hydroponic system (Bigfoot, American Hydroponics, Arcata, Calif.) in an Enconair growth chamber with a 16 hr photoperiod at a light intensity of 140 µmol m−2 s−1 at plant height, and a 22° C. day temperature (19° C. night). Plants were supplied with nutrient solution containing 2 mM or 10 mM nitrate through a pumping system once every 8 hrs.

Leaf 7 (the seventh leaf formed by each plant) was tagged with thread 21 days after sowing ("days after sowing" abbreviation: DAS). Collection of leaf 7 was started at 22 DAS and continued every other day until 42 DAS, for a total of 11 time points. Sampling of siliques started when siliques reached stage 16 (floral organs withering) and 2, 4, 6, and 8 days post stage 16, for a total of five time points. At each time point, leaf 7 and siliques were harvested from 10-12 plants and eight plants, respectively, with plants being selected to minimize any potential effects of position within the hydroponic tub and growth room.

RNA Isolation.

Leaves were pulverized in liquid nitrogen with a mortar and pestle. Approximately 100 µl of frozen tissue was combined with buffer RA1 with 1% β-mercaptoethanol (NucleoSpin® 96 RNA, Macherey-Nagel, Bethlehem, Pa.), and total RNA was isolated according to the manufacturer's specifications and implemented as a custom method on a Biomek® FX$^P$ (Beckman Coulter, Brea, Calif.) liquid handling workstation. In some cases, RNA yields were too low to satisfy the target of 2 µg for making adapter libraries. In these cases a second aliquot of 100 µL tissue was taken to perform an additional RNA extraction. RNA from the second extraction was used if the yield was sufficient. Otherwise, RNA was pooled from both extractions.

Silique RNA was extracted following a modified protocol (Meng and Feldman, 2010, *Biotechnol. J.* 5: 183-186). This procedure employs a modified, high pH (pH 9.5) extraction buffer. An RNAeasy® kit (Quiagen, Hilden, Germany) was subsequently used to purify the RNA.

Sequence Library Creation.

The starting total RNA concentration was measured using a NanoDrop® Spectrophotometer (Thermo Scientific™, Waltham, Mass.) and 2 µg of total RNA was used as the entry point to the TruSeq RNA Sample Prep method (15008136_A, Illumina®, San Diego, Calif.). All steps were performed according to manufacturer specifications as indicated in the High-Throughput (HT) Protocol, but implemented as a custom method on a Biomek $FX^P$ liquid handling workstation. In brief, poly-A containing mRNA molecules were purified using poly-T oligo-attached magnetic beads (2-rounds), fragmented with heat to a size of 120-200 bp, and then reverse transcribed using random hexamer primers. Double stranded cDNA was produced and indexed adapters were attached by ligation (Illumina, Inc.). Library size distribution was assessed by capillary gel electrophoresis, and then normalized based on quantification based on absorbance, fluorescence and quantitative polymerase chain reaction (qPCR) using primers targeting the adapter sequences.

Sequencing.

Normalized libraries were pooled proportionally based on the results of the RT-PCR quantification and prepared for sequencing. Cluster formation on the flowcell was performed with the Illumina Cluster Station system and the TruSeq SR Cluster Kit v5 (Illumina). Flowcells were sequenced on the Genome Analyzer IIx (GAIIx) system using TruSeq SBS Kit v5 (Illumina) to produce single end 29 bp reads, plus a 7-cycle index read. At least 15 million reads per sample was acquired.

Data Processing.

Output from the GAIIx was pre-processed using Illumina's CASAVA software v1.8.1 to produce one file of short-read basecall profiles for each sample. Short reads in basecall profiles were aligned to transcript elements (N=41671) in the genomic reference *Arabidopsis* transcriptome (TAIR10_GFF3_genes.gff) using the TopHat program v2.0.4 with default parameters. Resulting TopHat alignment profiles were converted to SAM format using SAMTools v0.1.18. For each sample, absolute expression profiles were quantified using HTSeq v0.5.3p9 to produce counts for each "gene", aggregating across all aligned transcripts of the gene as structurally defined in the GFF. HTSeq was run in "union" mode in non-strand specific fashion. Gene expression profiles were then analyzed with EdgeR v3.0 to account for batch and treatment effects. Only genes that had more than two reads per million total reads in three or more samples were modeled.

Contrasts were created to compare the combinations of experimental factors against appropriate controls using a log-likelihood ratio test with p-values calculated using a $\chi 2$ distribution. Since these analyses produce results using many statistical tests, a Benjamini-Hochberg false discovery rate (FDR) multiple test correction was applied to p-values within each profile. To be considered differentially expressed between experimental conditions, a given gene was required to show at least a 1.3 fold difference of expression with a statistical significance of p-FDR<0.05.

Selection of Genes.

The transcript profiles of leaves at each of the 11 time points (22, 24, 26, 28, 30, 32, 34, 36, 38, 40 and 42 DAS) and silique (stage 16, 2, 4, 6 and 8 days post stage 16) were obtained, comparisons were made (i) between plants supplied with low and high nitrate at matched time point and (ii) against the initial time point (22 DAS and stage 16 for leaf and silique, respectively). The expression profiles of the low N and high N grown plants were relatively similar until 30 DAS, corresponding to the time when seed filling began, when a large number of genes began to be differentially expressed in low N conditions and visual evidence of senescence initiation was first noted in leaf 7 in low N. The resulting data were analyzed through a number of computational approaches, e.g., SplineCluster (Heard et al., 2006, *J. Am. Statist. Assoc.* 101: 18-29; Heard 2011, *J. Comput. Graph. Stat.* 20: 920-936, Cornet (cornet.psb.ugent.be/), Gene Ontology analysis and various network inference approaches) to identify potential regulators of NUE and NUpE. Differentially expressed regulatory genes (transcription factors, kinases, phosphatases, RING ubiquitin ligases) were also individually examined. Two types of genes were selected for experimental analysis:

1) Regulatory genes consistently more highly expressed in leaves of plants grown in low N than in leaves of plants grown in high N before 30 DAS. These are candidate genes for up-regulation in leaves, roots, vascular tissue, or whole plants to improve nitrogen uptake and/or assimilation.

2) Regulatory genes consistently more highly expressed in leaves of plants grown in high N than in leaves of plants grown in low N before 30 DAS. These are candidate genes for down-regulation leaves, roots, vascular tissue, or whole plants to improve nitrogen uptake and/or assimilation.

Example II. Identification of Regulators of UI and NUpE Through Whole Plant Soil-Based or Plate-Based Screening Assays Plants grown in plate-based studies or under normal growth conditions in soil may exhibit characteristics of enhanced nitrogen uptake efficiency or nitrogen use efficiency. For example, plants overexpressing a particular gene that are larger or darker green compared to control plants may be able to utilize nitrogen more effectively. In this way, large numbers of genes may be rapidly screened by examining changes in biomass, chlorophyll and nitrogen content.

Plant Growth Conditions for Plate-Based Assays.

Seeds from *Arabidopsis* lines overexpressing various genes were chlorine gas sterilized and stratified at 4° C. for three days and spread onto plates containing a sucrose-based media augmented with vitamins (80% MS+Vit, 1% sucrose, 0.65% Phytoblend™ agar) and kanamycin (3.5 mg/L). The media on these plates can be amended by altering the sucrose or nitrogen levels to alter seedling root and shoot development (for example, see Malamy and Ryan, 2001, *Plant Physiol.* 127: 899-909, Zhang and Forde, 2000, *J. Exp. Bot.* 51:51-59, Watch-Liu et al., 2006, *Ann. Bot.* 97: 875-881, Gifford et al., 2013, *PLoS Genet.* 9(9): e1003760. doi:10.1371/journal.pgen.1003760). The effect of the gene being overexpressed may be determined by growing control and overexpressing lines on the same plate and observing if root and shoot architecture (e.g. root length, root branching, dark green rosette leaves) are altered.

Plant Growth Conditions for Soil Based Experiments.

Seeds from *Arabidopsis* lines overexpressing various genes were chlorine gas sterilized using a standard protocol and spread onto plates containing a sucrose-based media augmented with vitamins (80% MS+Vit, 1% sucrose, 0.65%

PhBL) and either kanamycin (80% MS+Vit, 1% sucrose, 0.65% Phytoblend agar, kanamycin 3.5 mg/L) or sulfonamide (80% MS+Vit, 1% sucrose, 0.65% Phytoblend agar, asulam (1.5 mg/L) where selection was required. Seeds were stratified in the dark on plates, at 4° C. for three days, then moved to a walk-in growth chamber (Conviron MTW120, Conviron Controlled Environments Ltd, Winnipeg, Manitoba, Canada) running at a 10 h photoperiod at a photosynthetic photon flux of ca. 200 μmol m$^{-2}$ s$^{-1}$ at plant height and a photoperiod/night temperature regime of 22° C./19° C. After seven days of light exposure, seedlings were transplanted into 164 ml volume pots containing autoclaved ProMix® soil augmented with beneficial organisms for pest and disease control. All pots were returned to the same growth-chamber and were left standing in water, covered with a lid for the first seven days. This protocol kept the soil moist during this period. Seven days after transplanting, lids were removed and a watering and nutrition regime was begun. All plants received a fertilizer treatment once a week (80% Peter's NPK fertilizer), and water on two other days.

Rosette Biomass and Chemical Analysis for Soil Based Experiments.

The dry weight of whole *Arabidopsis* rosettes was measured after being dried down at 80° C. for 24 hours, a time found to be sufficient to reach constant weight. Samples were taken after 35 to 38 days growth, and used as an assay of aboveground productivity at growth light. Typically, five replicate rosettes were sampled per *Arabidopsis* line being screened. After weighing, the five rosettes sampled for each line screened were pooled together and ground to a fine powder. The pooled sample generated was sub-sampled and ca. 4 μg samples were analyzed for C and N using an elemental analyzer.

Example III. Production of Transgenic Plants

The above-identified regulatory genes may combined with tissue-specific or constitutive promoters and be used to create constructs to transform plants. Transformed plants may be prepared using the following methods, although these examples are not intended to limit the description or claims.

Transformation.

Transformation of *Arabidopsis* is typically performed by an *Agrobacterium*-mediated protocol based on the method of Bechtold and Pelletier, 1998, *Methods Mol. Biol.* 82:259-266.

Plant Preparation.

*Arabidopsis* seeds are sown on mesh covered pots. The seedlings are thinned so that 6-10 evenly spaced plants remain on each pot 10 days after planting. The primary bolts are cut off a week before transformation to break apical dominance and encourage axillary shoots to form. Transformation is typically performed at 4-5 weeks after sowing.

Bacterial Culture Preparation.

*Agrobacterium* stocks are inoculated from single colony plates or from glycerol stocks and grown with the appropriate antibiotics and grown until saturation. On the morning of transformation, the saturated cultures are centrifuged and bacterial pellets are re-suspended in Infiltration Media (0.5× MS, 1×B5 Vitamins, 5% sucrose, 1 mg/ml benzylaminopurine riboside, 200 μl/L Silwet L77) until an A600 reading of 0.8 is reached.

Transformation and Seed Harvest.

The *Agrobacterium* solution is poured into dipping containers. All flower buds and rosette leaves of the plants are immersed in this solution for 30 seconds. The plants are laid on their side and wrapped to keep the humidity high. The plants are kept this way overnight at 22° C. and then the pots are unwrapped, turned upright, and moved to the growth racks.

The plants are maintained on the growth rack under 24-hour light until seeds are ready to be harvested. Seeds are harvested when 80% of the siliques of the transformed plants are ripe (approximately five weeks after the initial transformation). This seed is deemed T0 seed, since it is obtained from the T0 generation, and is later plated on selection plates (kanamycin, sulfonamide or glyphosate). Resistant plants that are identified on such selection plates comprise the T1 generation.

For polynucleotides encoding polypeptides used in these experiments, RT-PCR may be performed to confirm the ability of cloned promoter fragments to drive expression of the polypeptide transgene in plants transformed with the vectors.

T1 plants transformed with promoter-TF combinations comprised within a nucleic acid construct are subjected to morphological analysis. Promoters that produce a substantial amelioration of the negative effects of TF overexpression are subjected to further analysis by propagation into the T2 generation, where the plants are analyzed for an altered trait relative to a control plant.

Example IV. Evaluating Transgenic *Arabidopsis* Usage Index (UI) and Nitrogen Uptake Efficiency (NupE) Under Limiting or Ample Nitrogen Conditions Using Whole Plant Assays Plant Growth and Tissue Isolation.

Transgenic seeds were surface sterilized using chlorine gas, plated on selective media, and stratified for three days at 4° C. in the dark. Plates were incubated at 22° C. under a light intensity of approximately 100 μmole m$^{-2}$ sec$^{-1}$ for seven days (Conviron ATV-26 growth chamber) under a L:D 10:14 regime. Seedlings were then transplanted into square pots (60 mm×60 mm) containing fritted clay topped with a small (10 mm) layer of medium particle sized sand and kept covered with a plastic dome for another seven days to maintain humidity while they became established. Plants are grown in this soil mixture under fluorescent lights, at a light intensity of approximately 100 μmole m$^{-2}$ sec$^{-1}$ and a temperature of 22° C. (L:D 10:14). Plants were cultivated under limiting nitrogen (2 mM nitrate) or ample nitrogen (10 mM nitrate) conditions. Phosphate (0.25 mM), sulfate (0.25 mM), magnesium (0.25 mM), and sodium (0.20 mM) were present in both solutions at the same concentration. The difference between low and high N solutions affects only potassium (5.25 mM and 2.75 mM in high and low N solutions, respectively), calcium (2.50 mM and 0.50 mM, respectively), and chloride ions (0.25 mM and 0.70 mM, respectively). Pots were watered three times per daily every eight h using a commercial ebb and flow hydroponic system (Bigfoot, American Hydroponics, Arcata Calif.).

$^{15}$N Labeling and Harvest.

$^{15}$N uptake was estimated 32 days after sowing when plants were still vegetative. The unlabelled watering solution was replaced by a $^{15}$N-containing solution that had the same nutrient composition except that $^{14}$NO$_3$ was replaced by $^{15}$NO$_3$ at 2.5% enrichment. All pots were watered for 24 h by immersing the base of the pot with a volume of labeled solutions sufficient to cover the lower 35 mm of the pot. After 24 h, the rosette was separated from its root to stop $^{15}$N uptake. Rosettes were then dried and their dry weight was determined. Four to six replicates were harvested for uptake and remobilization experiments.

Determination of Total Nitrogen Content and $^{15}N$ Abundance.

After drying and weighing each sample, material was ground in a bead mill to obtain a homogenous fine powder. A subsample of 2 to 3 mg was weighed into tin capsules to determine the total N content and $^{15}N$ abundance at the Stable Isotope Facility at UC Davis. Samples were analyzed for $^{15}N$ isotopes using a PDZ Europa ANCA-GSL elemental analyzer interfaced to a PDZ Europa 20-20 isotope ratio mass spectrometer (Sercon Ltd., Cheshire, UK). Samples were combusted at 1000° C. in a reactor packed with chromium oxide and silvered cobaltous/cobaltic oxide. Following combustion, oxides were removed in a reduction reactor (reduced copper at 650° C.). The helium carrier then flowed through a water trap (magnesium perchlorate). $N_2$ and $CO_2$ were resolved on a Carbosieve® GC column (65° C., 65 mL/min) before entering the IRMS. During analysis, samples were interspersed with several replicates of at least two different laboratory standards. These laboratory standards (selected to be compositionally similar to the samples being analyzed) were previously calibrated against NIST Standard Reference Materials (IAEA-N1, IAEA-N2, IAEA-N3, USGS-40, and USGS-41). A sample's preliminary isotope ratio is measured relative to reference gases analyzed with each sample. These preliminary values are finalized by correcting the values for the entire batch based on the known values of the included laboratory standards. The long term standard deviation is 0.3 per mil for $^{15}N$. The $^{15}N$ abundance was calculated as atom percent (A %=($^{15}N$)/($^{15}N+^{14}N$)) and for unlabeled plant controls (A %$_{control}$) was 0.3660. The $^{15}N$ enrichment (E %) of the plant material was then defined as E %=A %$_{sample}$-A %$_{control}$.

Determination of Nitrogen Related Parameters (Nitrogen Usage Index and Nitrogen Uptake Efficiency).

A number of traits related to nitrogen uptake and remobilization can be derived from tissue dry weight, tissue % nitrogen (% N), and tissue E %.

Usage Index (UI)

Usage index (UI)=tissue dry weight/N %

N uptake efficiency (NupE)

NupE=$^{15}N$/tissue dry weight=E %×N %×100

Example V. Experimental Results

This Example provides experimental observations for transgenic plants overexpressing GATA23, MYB50, AT2G43260, RBP45A, AtbHLH017, NF-YB4, ATL6, LSD1, WRKY17, ZAT11 and HMGB14, and results observed for improved nitrogen uptake. Two or three independent lines for each gene were evaluated for Usage Index (UI) and N uptake efficiency (NupE) under conditions of limiting and ample nitrogen as described above.

GATA23:

One GATA23 line showed a statistically significant increase in NupE when evaluated under limiting N conditions (150% of control). Two independent lines showed an increase in UI under ample N conditions (360% and 240% of control), including the same line that showed an improvement in NupE under limiting N conditions.

TABLE 4

Enhanced nitrogen uptake in plants ectopically expressing GATA23

| Gene Name | Event # | NupE Ave. | p val | % incr | UI Ave. | p val | % incr |
|---|---|---|---|---|---|---|---|
| Limiting nitrogen | | | | | | | |
| GATA23 | 1 | 72.0 | — | | 0.18 | — | |
| GATA23 | 2 | 72.4 | — | | 0.21 | — | |
| GATA23 | 3 | 88.4 | 0.087 | 150 | 0.20 | — | |
| Control | | 59.0 | | | 0.16 | | |
| Ample nitrogen | | | | | | | |
| GATA23 | 1 | 55.7 | — | | 0.25 | 0.000 | 360 |
| GATA23 | 2 | 55.5 | — | | 0.17 | | |
| GATA23 | 3 | 60.6 | — | | 0.17 | 0.098 | 240 |
| Control | | 56.9 | | | 0.07 | | |

MYB50.

One MYB50 line showed a statistically significant increase in NupE when evaluated under ample N conditions. Two independent MYB50 lines showed an increase in UI under limiting N conditions, and all three lines tested showed an improvement in UI under ample N conditions.

TABLE 5

Enhanced nitrogen uptake in plants ectopically expressing MYB50

| Gene Name | Event # | NupE Ave. | p val | % incr | UI Ave. | p val | % incr |
|---|---|---|---|---|---|---|---|
| Limiting nitrogen | | | | | | | |
| MYB50 | 1 | 62.8 | — | | 0.26 | 0.054 | 163 |
| MYB50 | 2 | 76.5 | — | | 0.25 | — | |
| MYB50 | 3 | 77.5 | — | | 0.27 | 0.010 | 169 |
| Control | | 59.0 | | | 0.16 | | |
| Ample nitrogen | | | | | | | |
| MYB50 | 1 | 62.3 | — | | 0.30 | 0.000 | 429 |
| MYB50 | 2 | 109.3 | 0.007 | 192 | 0.21 | 0.007 | 300 |
| MYB503 | 3 | 98.4 | — | | 0.28 | 0.090 | 400 |
| Control | | 56.9 | | | 0.07 | | |

AT2G43260:

Two independent AT2G43260_lines showed an increase in UI under limiting N conditions, and all three lines tested showed an improvement in UI under ample N conditions.

TABLE 6

Enhanced nitrogen uptake in plants ectopically expressing AT2G43260

| Gene Name | Event # | NupE Ave. | p val | % incr | UI Ave. | p val | % incr |
|---|---|---|---|---|---|---|---|
| Limiting nitrogen | | | | | | | |
| AT2G43260 | 1 | 64.7 | — | | 0.27 | 0.034 | 168 |
| AT2G43260 | 2 | 73.2 | — | | 0.23 | — | |
| AT2G43260 | 3 | 72.5 | — | | 0.33 | 0.000 | 206 |
| Control | | 59.0 | | | 0.16 | | |
| Ample nitrogen | | | | | | | |
| AT2G43260 | 1 | 64.7 | — | | 0.18 | 0.034 | 257 |
| AT2G43260 | 2 | 68.7 | — | | 0.18 | 0.052 | 257 |
| AT2G43260 | 3 | 62.5 | — | | 0.18 | 0.067 | 257 |
| Control | | 56.9 | | | 0.07 | | |

RBP45A:

All three independent RBP45A lines tested showed a significant increase in UI when grown under limiting N conditions, and one of these lines also showed a significant increase in UI under ample N conditions.

TABLE 7

Enhanced nitrogen uptake in plants ectopically expressing RBP45A

| Gene | Event | NupE | | | UI | | |
|---|---|---|---|---|---|---|---|
| Name | # | Ave. | p val | % incr | Ave. | p val | % incr |
| Limiting nitrogen | | | | | | | |
| RBP45A | 1 | 68.8 | — | | 0.36 | 0.000 | 225 |
| RBP45A | 2 | 85.4 | — | | 0.27 | 0.012 | 169 |
| RBP45A | 3 | 71.4 | — | | 0.26 | 0.031 | 162 |
| Control | | 59.0 | | | 0.16 | | |
| Ample nitrogen | | | | | | | |
| RBP45A | 1 | 63.5 | — | | 0.16 | — | |
| RBP45A | 2 | 65.1 | — | | 0.18 | 0.036 | 257 |
| RBP45A | 3 | 80.9 | — | | 0.12 | — | |
| Control | | 56.9 | | | 0.07 | | |

AtbHLH017:

All three independent AtbHLH017 lines tested showed a significant increase in UI when grown under limiting N conditions.

TABLE 8

Enhanced nitrogen uptake in plants ectopically expressing AtbHLH017

| Gene | Event | NupE | | | UI | | |
|---|---|---|---|---|---|---|---|
| Name | # | Ave. | p val | % incr | Ave. | p val | % incr |
| Limiting nitrogen | | | | | | | |
| AtbHLH017 | 1 | 65.5 | — | | 0.27 | 0.027 | 169 |
| AtbHLH017 | 2 | 57.8 | — | | 0.27 | 0.017 | 169 |
| AtbHLH017 | 3 | 65.2 | — | | 0.28 | 0.008 | 175 |
| Control | | 59.0 | | | 0.16 | | |
| Ample nitrogen | | | | | | | |
| AtbHLH017 | 1 | 70.8 | — | | 0.14 | — | |
| AtbHLH017 | 2 | 61.7 | — | | 0.12 | — | |
| AtbHLH017 | 3 | 82.8 | — | | 0.14 | — | |
| Control | | 56.9 | | | 0.07 | | |

NF-YB4:

One NF-YB4 line showed a significant increase in NupE when grown under ample N.

TABLE 9

Enhanced nitrogen uptake in plants ectopically expressing NFYB4

| Gene | Event | NupE | | | UI | | |
|---|---|---|---|---|---|---|---|
| Name | # | Ave. | p val | % incr | Ave. | p val | % incr |
| Limiting nitrogen | | | | | | | |
| NF-YB4 | 1 | 51.2 | — | | 0.13 | — | |
| NF-YB4 | 2 | 50.2 | — | | 0.08 | — | |
| NF-YB4 | 3 | 52.5 | — | | 0.09 | — | |
| Control | | 59.0 | | | 0.16 | | |
| Ample nitrogen | | | | | | | |
| NF-YB4 | 1 | 72.7 | — | | 0.09 | — | |
| NF-YB4 | 2 | 66.4 | — | | 0.08 | — | |
| NF-YB4 | 3 | 98.4 | 0.058 | 172 | 0.09 | — | |
| Control | | 56.9 | | | 0.07 | | |

ATL6:

Two independent ATL6 lines showed an increase in NupE under limiting N, and in UI under ample N conditions.

TABLE 10

Enhanced nitrogen uptake in plants ectopically expressing ATL6

| Gene | Event | NupE | | | UI | | |
|---|---|---|---|---|---|---|---|
| Name | # | Ave. | p val | % incr | Ave. | p val | % incr |
| Limiting nitrogen | | | | | | | |
| ATL6 | 1 | 93.3 | 0.026 | 158 | 0.22 | — | |
| ATL6 | 2 | 99.2 | 0.005 | 168 | 0.24 | — | |
| Control | | 59.0 | | | .16 | | |
| Ample nitrogen | | | | | | | |
| ATL6 | 1 | 89.2 | — | | 0.23 | 0.001 | 328 |
| ATL6 | 2 | 78.0 | — | | 0.25 | 0.000 | 357 |
| Control | | 56.9 | | | 0.07 | | |

LSD1:

Two independent LSD1 overexpressing lines showed an increase in NupE under both limiting and ample N conditions. One line also showed an increase in UI under limiting N.

TABLE 11

Enhanced nitrogen uptake in plants ectopically expressing LSD1

| Gene | Event | NupE | | | UI | | |
|---|---|---|---|---|---|---|---|
| Name | # | Ave. | p val | % incr | Ave. | p val | % incr |
| Limiting nitrogen | | | | | | | |
| LSD1 | 1 | 97.7 | 0.002 | 152 | 0.13 | — | |
| LSD1 | 2 | 111.0 | 0.000 | 173 | 0.23 | 0.000 | 176 |
| Control | | 64.0 | | | 0.13 | | |
| Ample nitrogen | | | | | | | |
| LSD1 | 1 | 118.8 | 0.008 | 152 | 0.19 | — | |
| LSD1 | 2 | 110.2 | 0.091 | 142 | 0.20 | — | |
| Control | | 77.6 | | | 0.12 | | |

WRKY17:

Three independent WRKY17 overexpressing lines showed a significant increase in NupE under limiting N conditions, and two of these lines also showed a significant increase under ample N. All three lines also showed an increase in UI under both limiting and ample N.

TABLE 12

Enhanced nitrogen uptake in plants ectopically expressing WRKY17

| Gene | Event | NupE | | | UI | | |
|---|---|---|---|---|---|---|---|
| Name | # | Ave. | p val | % incr | Ave. | p val | % incr |
| Limiting nitrogen | | | | | | | |
| WRKY17 | 1 | 100.3 | 0.000 | 157 | 0.30 | 0.000 | 231 |
| WRKY17 | 2 | 118.6 | 0.000 | 185 | 0.30 | 0.000 | 231 |
| WRKY17 | 3 | 110.9 | 0.000 | 173 | 0.33 | 0.000 | 254 |
| Control | | 64.0 | | | 0.13 | | |
| Ample nitrogen | | | | | | | |
| WRKY17 | 1 | 100.9 | — | | 0.23 | 0.033 | 192 |
| WRKY17 | 2 | 114.3 | 0.026 | 147 | 0.22 | 0.054 | 183 |
| WRKY17 | 3 | 114.8 | 0.023 | 148 | 0.23 | 0.040 | 192 |
| Control | | 77.6 | | | 0.12 | | |

ZAT11:

Three independent ZAT11 overexpressing lines showed a significant increase in NupE and UI under both limiting and ample N conditions.

TABLE 13

Enhanced nitrogen uptake in plants ectopically expressing ZAT11

| Gene Name | Event # | NupE | | | UI | | |
|---|---|---|---|---|---|---|---|
| | | Ave. | p val | % incr | Ave. | p val | % incr |
| Limiting nitrogen | | | | | | | |
| ZAT11 | 1 | 128.1 | 0.000 | 200 | 0.34 | 0.000 | 262 |
| ZAT11 | 2 | 130.1 | 0.000 | 203 | 0.32 | 0.000 | 246 |
| ZAT11 | 3 | 117.1 | 0.000 | 183 | 0.38 | 0.000 | 292 |
| Control | | 64.0 | | | 0.13 | | |
| Ample nitrogen | | | | | | | |
| ZAT11 | 1 | 115.4 | 0.019 | 149 | 0.25 | 0.007 | 208 |
| ZAT11 | 2 | 125.6 | 0.000 | 162 | 0.27 | 0.001 | 225 |
| ZAT11 | 3 | 146.6 | 0.000 | 189 | 0.28 | 0.000 | 233 |
| Control | | 77.6 | | | 0.12 | | |

HMGB14:

Three independent HMGB14 lines showed an increase in UI under limiting N conditions; one of these lines also showed an increase in UI under ample N conditions and an increase in NupE under limiting N conditions.

TABLE 14

Enhanced nitrogen uptake in plants ectopically expressing HMGB14

| Gene Name | Event # | NupE | | | UI | | |
|---|---|---|---|---|---|---|---|
| | | Ave. | p val | % incr | Ave. | p val | % incr |
| Limiting nitrogen | | | | | | | |
| HMGB14 | 1 | 100.4 | | | 0.22 | .019 | 157 |
| HMGB14 | 2 | 86.3 | | | 0.23 | .016 | 164 |
| HMGB14 | 3 | 149.9 | 0.001 | 178 | 0.20 | .088 | 143 |
| Control | | 84.2 | | | 0.14 | | |
| Ample nitrogen | | | | | | | |
| HMGB14 | 1 | 29.0 | | | 0.27 | | |
| HMGB14 | 2 | 27.8 | | | 0.28 | | |
| HMGB14 | 3 | 50.9 | | | 0.35 | .010 | 194 |
| Control | | 39.7 | | | 0.18 | | |

Example VI. Plant Transformation Methods

Crop species that overexpress polypeptides of the instant description may produce plants with increased photosynthetic resource use efficiency and/or yield. Thus, polynucleotide sequences listed in the Sequence Listing recombined into, for example, one of the expression vectors of the instant description, or another suitable expression vector, may be transformed into a plant for the purpose of modifying plant traits for the purpose of improving yield, quality, and/or photosynthetic resource use efficiency. The expression vector may contain a constitutive, tissue-enhanced or inducible promoter operably linked to the polynucleotide. The cloning vector may be introduced into a variety of plants by means well known in the art such as, for example, direct DNA transfer or *Agrobacterium tumefaciens*-mediated transformation.

Transformation of Monocots.

Cereal plants including corn, wheat, rice, sorghum, barley, or other monocots may be transformed with the present polynucleotide sequences, including monocot or eudicot-derived sequences such as those presented in the present Tables, cloned into a vector such as pGA643 and containing a kanamycin-resistance marker, and expressed constitutively under, for example, the CaMV35S or COR15 promoters, or with tissue-enhanced or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^{-9}$ cells of *Agrobacterium* containing the cloning vector for 3-10 minutes. The callus material is cultured on solid medium at 25° C. in the dark for several days. The calli grown on this medium are transferred to a Regeneration Medium. Transfers are continued every two to three weeks (two or three times) until shoots develop. Shoots are then transferred to Shoot-Elongation Medium every 2-3 weeks. Healthy looking shoots are transferred to Rooting Medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil, 1994. *Plant Mol. Biol.* 25: 925-937) such as corn, wheat, rice, sorghum (Cassas et al., 1993. *Proc. Natl. Acad. Sci. USA* 90: 11212-11216), and barley (Wan and Lemeaux, 1994. *Plant Physiol.* 104: 37-48). DNA transfer methods such as the microprojectile method can be used for corn (Fromm et al., 1990. *Bio/Technol.* 8: 833-839; Gordon-Kamm et al., 1990. *Plant Cell* 2: 603-618; Ishida, 1990. *Nature Biotechnol.* 14:745-750), wheat (Vasil et al., 1992. *Bio/Technol.* 10:667-674; Vasil et al., 1993. *Bio/Technol.* 11:1553-1558; Weeks et al., 1993. *Plant Physiol.* 102:1077-1084), and rice (Christou, 1991. *Bio/Technol.* 9:957-962; Hiei et al., 1994. *Plant J.* 6:271-282; Aldemita and Hodges, 1996. *Planta* 199: 612-617; and Hiei et al., 1997. *Plant Mol. Biol.* 35:205-218). For most cereal plants, embryogenic cells derived from immature scutellum tissues are the preferred cellular targets for transformation (Hiei et al., 1997. supra; Vasil, 1994. supra). For transforming corn embryogenic cells derived from immature scutellar tissue using microprojectile bombardment, the A188XB73 genotype is the preferred genotype (Fromm et al., 1990. *Bio/Technol.* 8: 833-839; Gordon-Kamm et al., 1990. supra). After microprojectile bombardment the tissues are selected on phosphinothricin to identify the transgenic embryogenic cells (Gordon-Kamm et al., 1990. supra). Transgenic plants from transformed host plant cells may be regenerated by standard corn regeneration techniques (Fromm et al., 1990. *Bio/Technol.* 8: 833-839; Gordon-Kamm et al., 1990. supra).

Transformation of Dicots.

It is now routine to produce transgenic plants using most eudicot plants (see U.S. Pat. No. 8,273,954 (Rogers et al.) issued Sep. 25, 2012; Weissbach and Weissbach, 1989. *Methods for Plant Molecular Biology*, Academic Press; Gelvin et al., 1990. *Plant Molecular Biology Manual*, Kluwer Academic Publishers; Herrera-Estrella et al., 1983. *Nature* 303: 209; Bevan, 1984. *Nucleic Acids Res.* 12: 8711-8721; and Klee, 1985. *Bio/Technology* 3: 637-642). Methods for analysis of traits are routine in the art and examples are disclosed above.

Numerous protocols for the transformation of tomato and soy plants have been previously described, and are well known in the art. Gruber et al., in Glick and Thompson, 1993. *Methods in Plant Molecular Biology and Biotechnology*. eds., CRC Press, Inc., Boca Raton, describe several expression vectors and culture methods that may be used for cell or tissue transformation and subsequent regeneration. For soybean transformation, methods are described by Mild et al., 1993. in *Methods in Plant Molecular Biology and Biotechnology*, p. 67-88, Glick and Thompson, eds., CRC Press, Inc., Boca Raton; and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., 1987. *Part. Sci. Technol.* 5:27-37; Sanford, 1993. *Methods Enzymol.* 217: 483-509; Christou et al., 1992. *Plant. J.* 2: 275-281; Klein et al., 1987. *Nature* 327: 70-73; U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al., 1991. *Bio/Technology* 9: 996-997); direct uptake of DNA into protoplasts using $CaCl_2$ precipitation, polyvinyl alcohol or poly-L-ornithine (see, for example, Hain et al., 1985. *Mol. Gen. Genet.* 199: 161-168; Draper et al., 1982. *Plant Cell Physiol.* 23: 451-458); liposome or spheroplast fusion (see, for example, Deshayes et al., 1985. *EMBO J.*, 4: 2731-2737; Christou et al., 1987. *Proc. Natl. Acad. Sci. USA* 84: 3962-3966); and electroporation of protoplasts and whole cells and tissues (see, for example, Donn et al. 1990. in *Abstracts of VIIth International Congress on Plant Cell and Tissue Culture IAPTC*, A2-38: 53; D'Halluin et al., 1992. *Plant Cell* 4: 1495-1505; and Spencer et al., 1994. *Plant Mol. Biol.* 24: 51-61) have been used to introduce foreign DNA and expression vectors into plants.

After a plant or plant cell is transformed (and the transformed host plant cell then regenerated into a plant), the transformed plant may propagated vegetatively or it may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al, 1986. In *Tomato Biotechnology*: Alan R. Liss, Inc., 169-178, and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 µM-naphthalene acetic acid and 4.4 µM 6-benzylaminopurine. The explants are then infected with a diluted overnight culture of *Agrobacterium tumefaciens* containing an expression vector comprising a polynucleotide of the instant description for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7, to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on ¹⁄₁₀ strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

*Eucalyptus* is now considered an important crop that is grown for example to provide feedstocks for the pulp and paper and biofuel markets. This species is also amenable to transformation as described in PCT patent publication WO/2005/032241.

*Crambe* has been recognized as a high potential oilseed crop that may be grown for the production of high value oils. An efficient method for transformation of this species has been described in PCT patent publication WO 2009/067398 A1.

Overnight cultures of *Agrobacterium tumefaciens* harboring the expression vector comprising a polynucleotide of the instant description are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Experimental Methods; Transformation of *Arabidopsis*.

Transformation of *Arabidopsis* is performed by an *Agrobacterium*-mediated protocol based on the method of Bechtold and Pelletier, 1998. Unless otherwise specified, all experimental work is performed using the Columbia ecotype.

Plant Preparation.

*Arabidopsis* seeds are gas sterilized and sown on plates with media containing 80% MS with vitamins, 0.3% sucrose and 1% Bacto™ agar. The plates are placed at 4° C. in the dark for the days then transferred to 24 hour light at 22° C. for seven days. After 7 days the seedlings are transplanted to soil, placing individual seedlings in each pot. The primary bolts are cut off a week before transformation to break apical dominance and encourage auxiliary shoots to form. Transformation is typically performed at 4-5 weeks after sowing.

Bacterial Culture Preparation.

*Agrobacterium* stocks are inoculated from single colony plates or from glycerol stocks and grown with the appropriate antibiotics until saturation. On the morning of transformation, the saturated cultures are centrifuged and bacterial pellets are re-suspended in Infiltration Media (0.5× MS, 1× Gamborg's Vitamins, 5% sucrose, 200 μl/L Silwet® L77) until an $A_{600}$ reading of 0.8 is reached.

Transformation and Harvest of Transgenic Seeds.

The *Agrobacterium* solution is poured into dipping containers. All flower buds and rosette leaves of the plants are immersed in this solution for 30 seconds. The plants are laid on their side and wrapped to keep the humidity high. The plants are kept this way overnight at 22° C. and then the pots are turned upright, unwrapped, and moved to the growth racks. In most cases, the transformation process is repeated one week later to increase transformation efficiency.

The plants are maintained on the growth rack under 24-hour light until seeds are ready to be harvested. Seeds are harvested when 80% of the siliques of the transformed plants are ripe (approximately five weeks after the initial transformation). This seed is deemed $T_0$ seed, since it is obtained from the $T_0$ generation, and is later plated on selection plates (either kanamycin or sulfonamide). Resistant plants that are identified on such selection plates comprise the T1 generation, from which transgenic seed comprising an expression vector of interest may be derived.

Example VII. Identification of Crop Plants with Enhanced Nitrogen Uptake

Evaluating Transgenic Crop Plants for Enhanced Nitrogen Use Efficiency and Nitrogen Uptake Efficiency (NupE) Under Field Conditions.

In field studies, the nitrogen use efficiency (NUE) in crop production systems can be computed using a number of methods (Table 15; Dobermann, 2005, digitalcommons.unl.edu/agronomyfacpub/316). In field studies, these parameters are either calculated based on differences in crop yield and total N uptake with aboveground biomass between fertilized plots and an unfertilized control (the "difference method") or by using $^{15}$N-labeled fertilizers to estimate crop and soil recovery of applied N. The time scale in these studies is usually one cropping season while the spatial scale for measurement is mostly a field or plot. Because each parameter can differ in its value in interpreting the data, field research on fertilizer-N efficiency should include measurements of several parameters to assess causes of variation in NUE. The "difference method" is simple and cost efficient procedure which makes it particularly suitable for field research. The use of labeled $^{15}$N to trace the fate of applied N is a precise but expensive method that is only applicable in scientific experiments and is not generally used in field studies.

TABLE 15

Agronomic indices of N use efficiency

| NUE index | Calculation | Interpretation |
|---|---|---|
| NUE - Nitrogen use efficiency (also called partial factor productivity of applied N ($PFP_N$) (kg harvest product per kg N applied) | $NUE = Y_N/F_N$ | Most important for farmers because it integrates the use efficiency of both indigenous and applied N resources: $NUE = (Y_0/F_N) + AE_N$ Increasing indigenous soil N ($Y_0$) and the efficiency of applied N ($AE_N$) are equally important for improving NUE Limited potential for identifying specific constraints or promising management strategies |
| $AE_N$ = Agronomic efficiency of applied N (kg yield increase per kg N applied) | $AE_N = (Y_N - Y_0)/F_N$ | $AE_N$ is the product of the efficiency of N recovery from applied N and the efficiency with which the plant uses each additional unit of N acquired: $AE_N = RE_N \times PE_N$ $AE_N$ can be increased by N, crop, and soil management practices that affect $RE_N$, $PE_N$, or both. |
| $RE_N$ = Crop recovery efficiency of applied N (kg increase in N uptake per kg N applied) | $RE_N = (U_N - U_0)/F_N$ | $RE_N$ depends on the congruence between plant N demand and the quantity of N released from applied N. $RE_N$ is affected by the N application method (amount, timing, placement, N form) as well as factors that determine the size of the crop N sink (genotype, climate, plant density, abiotic/biotic stresses). |

TABLE 15-continued

Agronomic indices of N use efficiency

| NUE index | Calculation | Interpretation |
|---|---|---|
| $PE_N$ = Physiological efficiency of applied N (kg yield increase per kg increase in N uptake from fertilizer) | $PE_N = (Y_N - Y_0)/(U_N - U_0)$ | $PE_N$ represents the ability of a plant to transform N acquired from fertilizer into economic yield (grain). $PE_N$ depends on genotypic characteristics (e.g., harvest index), environmental and management factors, particularly during reproductive growth. Low $PE_N$ suggests sub-optimal growth (nutrient deficiencies, drought stress, heat stress, mineral toxicities, pests). |

FN-amount of (fertilizer) N applied (kg ha-1)
YN-crop yield with applied N (kg ha-1)
Y0-crop yield (kg ha-1) in a control treatment with no N
UN-total plant N uptake in aboveground biomass at maturity (kg ha-1) in a plot that received N
U0-the total N uptake in aboveground biomass at maturity (kg ha-1) in a plot that received no N Example VIII. Embodiments of the Description The contents and teachings of the instant application and each of the information sources provided herein can be relied on and used to make and use embodiments of the instant disclosure. Although particular embodiments are described, equivalent embodiments may be used to practice the compositions and methods of the instant description, embodiments, and claims.

The instant disclosure pertains to, but is not limited by, the following embodiments:

1. A method of altering architecture or physiology of a root tissue or green tissue in a plant, comprising:
    (a) introducing into a plant cell a nucleic acid construct comprising a constitutive, or a tissue-enhanced promoter that preferentially regulates expression of a polypeptide in a root, root cap, root meristem, root vasculature, vascular, and/or green tissue, wherein:
        said polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131 or SEQ ID NO: 2263 to 2312;
        wherein said regulation of expression of the polypeptide increases nitrogen uptake, assimilation, nitrogen uptake efficiency (NUpE), nitrogen usage index (UI), and/or seed yield in the transgenic plant as compared to a control or reference plant that does not comprise the a nucleic acid construct; and
    b. optionally, identifying a transgenic plant that has greater nitrogen uptake, assimilation, nitrogen uptake efficiency (NUpE), nitrogen usage index (UI), and/or greater seed yield, as compared to a control or reference plant.

2. A method for producing a plant that has enhanced nitrogen uptake, assimilation, nitrogen uptake efficiency (NUpE), nitrogen usage index (UI), and/or seed yield, the method comprising:
    (a) providing a plant with a nucleic acid construct comprising a constitutive promoter, or a tissue-enhanced promoter that preferentially regulates expression of a polypeptide in a root, root cap, root meristem, root vasculature, vascular, and/or green tissue, wherein:
        said polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131 or SEQ ID NO: 2263 to 2312;
        wherein said regulation of expression of the polypeptide increases nitrogen uptake in the transgenic plant as compared to a control or reference plant that does not comprise the a nucleic acid construct; and
    b. optionally, identifying a transgenic plant that has greater nitrogen uptake, assimilation, nitrogen uptake efficiency (NUpE), nitrogen usage index (UI), and/or greater seed yield, as compared to a control or reference plant.

3. The method of embodiment 2, wherein said providing the plant with the nucleic acid construct is accomplished by transforming a plant with the nucleic acid construct.

4. The method of embodiment 2, wherein said providing the plant with the nucleic acid construct is accomplished by crossing the plant with a plant that comprises the nucleic acid construct.

5. A method for producing a plant that has enhanced nitrogen uptake, assimilation, nitrogen uptake efficiency (NUpE), nitrogen usage index (UI), and/or greater seed yield in the plant or a part of the plant comprising:
   a. providing a constitutive promoter, or a root, root cap, root meristem, root vasculature, vascular, and/or green tissue-enhanced promoter that is capable of up-regulating gene expression in the root, root cap, root meristem, root vasculature, vascular, and/or green tissue structure, organ, or plant part of the plant;
   b. providing a suppressor of gene expression capable of suppressing expression of an endogenous polynucleotide and its encoded endogenous polypeptide;
      wherein said polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131 or SEQ ID NO: 2263 to 2312;
   c. providing a target plant with at least one nucleic acid construct to produce a transgenic plant, wherein the at least one nucleic acid construct comprises the constitutive or tissue-enhanced promoter and the suppressor of gene expression;
      wherein the tissue-enhanced promoter increases expression of the suppressor of gene expression in the structure, organ, or plant part of the transgenic plant of the transgenic plant, which results in decreased expression of the endogenous polynucleotide and its encoded endogenous polypeptide; and said decreased expression of the endogenous polypeptide increases nitrogen uptake, assimilation, nitrogen uptake efficiency (NUpE), nitrogen usage index (UI), and/or seed yield in the transgenic plant as compared to a control or reference plant that does not comprise the a nucleic acid construct; and
   d. optionally, identifying a transgenic plant that has greater nitrogen uptake, assimilation, nitrogen uptake efficiency (NUpE), nitrogen usage index (UI), and/or greater seed yield, as compared to the control or reference plant.

6. The method of embodiment 5, wherein the suppressor of gene expression is an RNAi (RNA interference) molecule, a small interfering RNA (siRNA) molecule, a small hairpin RNA (shRNA) molecule, a microRNA (miRNA) molecule, an antisense molecule, a cosuppression directing nucleic acid, a nucleic acid encoding a ribozyme, a nucleic acid encoding a deoxyribozyme (DNAzyme), a nucleic acid encoding a transcription factor suppressor, or a triple helix oligonucleotide that decreases the expression of the polynucleotide.

7. The method of embodiment 5, wherein the tissue-enhanced promoter is selected from the group consisting of SEQ ID NOs: 2313 to 2372.

8. A method for producing a plant that has enhanced nitrogen uptake in the plant or a part of the plant, comprising:
   a. growing a plant in a medium containing:
      a limiting concentration of nitrogen that limits growth of the plant; or an ample concentration of nitrogen that does not limit growth of the plant;
   b. identifying a polypeptide the expression of which is higher in a part of the plant including a root, root cap, root meristem, root vasculature, vascular, leaf, and/or green tissue structure or organ of a nitrogen-limited plant grown in the limiting concentration of nitrogen than in a corresponding root, root cap, root meristem, root vasculature, vascular, leaf, and/or green tissue structure or organ of a nitrogen-ample plant grown in the ample concentration of nitrogen;
   d. identifying a polynucleotide that encodes the polypeptide;
   c. identifying a constitutive promoter, or a root, root cap, root meristem, root vasculature, vascular, and/or green tissue-enhanced promoter that is capable of up-regulating protein expression in a root, root cap, root meristem, root vasculature, vascular, leaf, and/or green tissue structure or organ;
   e. introducing into a target plant at least one recombinant nucleic acid construct to produce a transgenic plant, and the at least one recombinant nucleic acid construct comprises the polynucleotide and the constitutive or tissue-enhanced promoter;
      wherein the tissue-enhanced promoter regulates transcription of the polynucleotide, and said transcriptional regulation is preferentially enhanced in the root, root cap, root meristem, root vasculature, vascular, and/or green tissue structure or organ of the transgenic plant;
      wherein the preferentially enhanced expression of the polypeptide in the transgenic plant or in the root, root cap, root meristem, root vasculature, vascular, and/or green tissue structure or organ of the transgenic plant increases nitrogen uptake, assimilation, nitrogen uptake efficiency (NUpE), nitrogen usage index (UI), and/or seed yield in the transgenic plant as compared to a control or reference plant that does not comprise the a nucleic acid construct; and
   f. optionally, selecting a transgenic plant that has greater nitrogen uptake, assimilation, nitrogen uptake efficiency (NUpE), nitrogen usage index (UI), and/or greater seed yield than the control plant.

9. A method for producing a plant that has enhanced nitrogen uptake in the plant or a part of the plant, comprising:
   a. growing a plant in a medium containing:
      a limiting concentration of nitrogen that limits growth of the plant; or an ample concentration of nitrogen that does not limit growth of the plant;
   b. identifying a polypeptide the expression of which is lower in a part of the plant including a root, root cap, root meristem, root vasculature, vascular, leaf, and/or green tissue structure or organ of a nitrogen-limited plant grown in the limiting concentration of nitrogen than in a corresponding root, root cap, root meristem, root vasculature, vascular, leaf, and/or green tissue structure or organ of a nitrogen-ample plant grown in the ample concentration of nitrogen;
   d. identifying a polynucleotide that encodes the polypeptide;

c. identifying a constitutive promoter, or a root, root cap, root meristem, root vasculature, vascular, and/or green tissue-enhanced promoter that is capable of up-regulating protein expression in a root, root cap, root meristem, root vasculature, vascular, leaf, and/or green tissue structure or organ;

e. introducing into a target plant at least one recombinant nucleic acid construct to produce a transgenic plant, and the at least one recombinant nucleic acid construct comprises the polynucleotide and the constitutive or tissue-enhanced promoter;

wherein the tissue-enhanced promoter regulates transcription of the polynucleotide, and said transcriptional regulation is preferentially enhanced in the root, root cap, root meristem, root vasculature, vascular, and/or green tissue structure or organ of the transgenic plant;

wherein the preferentially enhanced expression of the polypeptide in the transgenic plant or in the root, root cap, root meristem, root vasculature, vascular, and/or green tissue structure or organ of the transgenic plant increases nitrogen uptake, assimilation, nitrogen uptake efficiency (NUpE), nitrogen usage index (UI), and/or seed yield in the transgenic plant as compared to a control or reference plant that does not comprise the a nucleic acid construct; and f. optionally, selecting a transgenic plant that has greater nitrogen uptake, assimilation, nitrogen uptake efficiency (NUpE), nitrogen usage index (UI), and/or greater seed yield than the control plant.

10. The method of embodiment 8 or embodiment 9, wherein the limiting concentration of nitrogen in the medium is a total nitrogen content of 2 mM nitrogen and the ample concentration of nitrogen is a total nitrogen content of 10 mM nitrogen.

11. The method of embodiment 8, embodiment 9, or embodiment 10, wherein the polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131

12. A method for enhancing nitrogen uptake in a crop plant, the method comprising:

providing a transgenic crop plant that comprises at least one nucleic acid construct, wherein the nucleic acid construct comprises a promoter and a polynucleotide; and the promoter is a constitutive promoter or a root, root cap, root meristem, root vasculature, vascular, or green tissue-enhanced promoter;

wherein the polynucleotide encodes a polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131; and wherein the promoter enhances expression of the polynucleotide in the transgenic crop plant, or preferentially enhances expression of the polynucleotide in a root, root cap, root meristem, root vasculature, vascular, and/or green tissue structure or organ of the transgenic crop plant, and said preferential enhancement of expression increases nitrogen uptake in the transgenic crop plant relative to a control or reference plant that does not comprise the a nucleic acid construct.

13. A method for enhancing nitrogen uptake, assimilation, nitrogen uptake efficiency (NUpE), nitrogen usage index (UI), and/or seed yield in a crop plant, the method comprising:

providing a transgenic crop plant that comprises at least one recombinant nucleic acid construct, wherein the nucleic acid construct comprises a constitutive promoter or a root, root cap, root meristem, root vasculature, vascular, and/or green tissue-enhanced promoter, and a suppressor of gene expression capable of suppressing expression of an endogenous polynucleotide;

wherein the suppressor of gene expression inhibits expression of the polynucleotide and its encoded endogenous polypeptide, and the endogenous polypeptide is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 90%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or about 100% identical to SEQ ID NO:2n, where n=1 to 1131 or SEQ ID NO: 2263-2312; and wherein the constitutive or tissue-enhanced promoter increases expression of the suppressor of gene expression in the transgenic plant or the part of the transgenic plant, which results in decreased expression of the endogenous polynucleotide and its encoded endogenous polypeptide; and said decreased expression of the endogenous polypeptide increases nitrogen uptake, assimilation, nitrogen uptake efficiency (NUpE), nitrogen usage index (UI), and/or seed yield in the transgenic plant relative to the control plant.

14. The method of embodiment 13, wherein the suppressor of gene expression is an RNAi (RNA interference) molecule, a small interfering RNA (siRNA) molecule, a small hairpin RNA (shRNA) molecule, a microRNA (miRNA) molecule, an antisense molecule, a cosuppression directing nucleic acid, a nucleic acid encoding a ribozyme, a nucleic acid encoding a deoxyribozyme (DNAzyme), a nucleic acid encoding a transcription factor suppressor, or a triple helix oligonucleotide that decreases the expression of the polynucleotide.

15. The method of any of embodiments 13 or 14, wherein the plant has higher nitrogen uptake, assimilation, nitrogen uptake efficiency (NUpE), nitrogen usage index (UI), and/or seed yield.

16. The method of any of embodiments 13 to 15, wherein the tissue-enhanced promoter is selected from the group consisting of SEQ ID NOs: 2313 to 2349 or a promoter listed in Table 3.

17. A recombinant nucleic acid construct comprising a root, root cap, root meristem, root vasculature, vascular, and/or green tissue-enhanced promoter selected from the group consisting of SEQ ID NOs: 2313 to 2372;
    wherein the promoter regulates expression of a polynucleotide that inhibits expression of an endogenous polypeptide that is at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or 96%, at least 97%, at least 98%, or at least 99%, or about 100% identical to SEQ ID NO:2n, where n=1 to 1131, or to SEQ ID NO 2263 to 2312.

18. A transgenic crop plant produced by the method of any of embodiments 1 to 16 or comprising a recombinant nucleic acid construct of embodiment 17, wherein the transgenic plant has enhanced nitrogen uptake, assimilation, nitrogen uptake efficiency (NUpE), nitrogen usage index (UI), and/or seed yield, as compared to the control or reference plant.

19. The transgenic crop plant of embodiment 18, wherein the transgenic plant is selected from the group consisting of: a non-leguminous plant, a monocot plant, a cereal plant, a maize (corn) plant, a rice plant, a wheat plant, a barley plant, a sorghum plant, a millet plant, an oat plant, a triticale plant, a rye plant, a buckwheat plant, a fonio plant, and a *quinoa* plant.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description fall within the scope of the claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10047372B1). An electronic copy of the "Sequence Listing" will also be available from the USPTO upon request and payment of the fee set forth in 37 CFR 1.19(b)(3).

What is claimed is:

1. A method of altering architecture or physiology of a green tissue in a plant, comprising:
    (a) introducing into a plant cell a nucleic acid construct comprising a tissue-enhanced promoter consisting of the nucleic acid sequence set forth in SEQ ID NO: 2324, that preferentially regulates expression of a polypeptide having the amino acid sequence set forth in SEQ ID NO: 76 in a green tissue,
    wherein regulation of expression of the polypeptide increases nitrogen uptake, assimilation, nitrogen uptake efficiency (NUpE), nitrogen usage index (UI), and/or seed yield in a transgenic plant comprising the plant cell as compared to a control or reference plant that does not comprise the nucleic acid construct; and
    (b) optionally, identifying the transgenic plant comprising the plant cell.

2. A method for producing a plant that has enhanced nitrogen uptake, assimilation, nitrogen uptake efficiency (NUpE), nitrogen usage index (UI), and/or seed yield, the method comprising:
    (a) providing a plant with a nucleic acid construct comprising a tissue-enhanced promote consisting of the nucleic acid sequence set forth in SEQ ID NO: 2324, that preferentially regulates expression of a polypeptide having the amino acid sequence set forth in SEQ ID NO: 76 in a green tissue,
    wherein regulation of expression of the polypeptide increases nitrogen uptake in a transgenic plant comprising the plant cell as compared to a control or reference plant that does not comprise the nucleic acid construct; and
    (b) optionally, identifying the transgenic plant comprising the plant cell.

3. The method of claim 2, wherein the providing a plant with a nucleic acid construct comprises transforming the plant with the nucleic acid construct.

4. The method of claim 2, wherein the providing a plant with a nucleic acid construct comprises crossing the plant with a second plant that comprises the nucleic acid construct.

* * * * *